United States Patent [19]
Duggan et al.

[11] Patent Number: 5,658,929
[45] Date of Patent: *Aug. 19, 1997

[54] SULFONAMIDE FIBRINOGEN RECEPTOR ANTAGONISTS

[75] Inventors: Mark E. Duggan, Narberth; Melissa S. Egbertson, Ambler; Wasyl Halczenko, Hatfield; George D. Hartman, Lansdale; William L. Laswell, Perkasie, all of Pa.

[73] Assignee: Merck & Co., Inc., Rahway, N.J.

[ * ] Notice: The term of this patent shall not extend beyond the expiration date of Pat. No. 5,292,756.

[21] Appl. No.: 505,417

[22] Filed: Jul. 21, 1995

Related U.S. Application Data

[60] Continuation of Ser. No. 168,897, Dec. 16, 1993, abandoned, which is a division of Ser. No. 860,747, Mar. 25, 1992, Pat. No. 5,292,756, which is a continuation-in-part of Ser. No. 750,647, Aug. 30, 1991, abandoned, which is a continuation-in-part of Ser. No. 589,130, Sep. 27, 1990, abandoned.

[51] Int. Cl.$^6$ .................. A61K 31/445; C07D 211/22
[52] U.S. Cl. ............................. 514/317; 546/237
[58] Field of Search ............... 546/22, 232, 268, 546/193, 216, 275, 208, 218, 276, 209, 221, 210, 212, 222, 225, 281, 213, 256; 514/318, 326, 331, 332, 333, 336, 340, 341, 342, 343, 183, 210, 255, 374, 376, 381, 383, 297, 401, 422

[56] References Cited

U.S. PATENT DOCUMENTS

| | | | |
|---|---|---|---|
| 4,004,008 | 1/1977 | Makovec et al. | 514/235.5 |
| 4,098,889 | 7/1978 | Dunbar | 514/239.2 |
| 4,122,255 | 10/1978 | Krapcho et al. | 542/421 |
| 4,243,807 | 1/1981 | Friebe et al. | 546/232 |
| 4,622,331 | 11/1986 | Jozic | 514/331 |
| 4,977,165 | 12/1990 | Oinuma et al. | 514/318 |
| 5,023,233 | 6/1991 | Nutt et al. | 514/11 |
| 5,030,654 | 7/1991 | Barnish et al. | 514/510 |
| 5,061,693 | 10/1991 | Nutt et al. | 514/17 |
| 5,064,814 | 11/1991 | Klein et al. | 514/18 |
| 5,288,490 | 2/1994 | Budzynski et al. | 424/94.64 |

FOREIGN PATENT DOCUMENTS

| | | |
|---|---|---|
| 0 004 011 | 2/1979 | European Pat. Off. . |
| 0 381 033 | 8/1990 | European Pat. Off. . |
| 0 384 362 | 8/1990 | European Pat. Off. . |
| 0 449 079 | 3/1991 | European Pat. Off. . |

OTHER PUBLICATIONS

Hsia et al. "A comparison between heparin and low–dose aspirin as adjunctive therapy with tissue plaminogen activator for acute myocardial infarction" N. Eng. J. Med. v. 323 p. 1433–1437 Nov. 1990.

Merck Index, Tiropramide, 10th Ed., paragraph 9301 (1979).

Ruoslahti et al., Science, vol. 238, pp. 491–497 (1987).

Shebuski, R.J., "Principles Underlying the Use of Conjunctive Agents with Plasminogen Activators", Annals New York Academy of Sciences, vol. 667, pp. 382–394 (1991).

*Primary Examiner*—Ceila Chang
*Attorney, Agent, or Firm*—Richard S. Parr; Melvin Winokur

[57] ABSTRACT

A series of non-peptide derivatives that are antagonists of the fibrinogen IIb/IIIa receptor and thus are platelet anti-aggregation compounds useful in the prevention and treatment of diseases caused by thrombus formation.

4 Claims, No Drawings

SULFONAMIDE FIBRINOGEN RECEPTOR ANTAGONISTS

CROSS-REFERENCE

This is a continuation of Ser. No. 08/168,897, filed Dec. 16, 1993, which is a division of application Ser. No. 07/860,747, filed Mar. 25, 1992, now U.S. Pat. No. 5,292,756, which is a continuation-in-part of U.S. Ser. No. 07/750,647, filed Aug. 30, 1991, now abandoned, which is a continuation-in-part of U.S. Ser. No. 07/589,130, filed Sep. 27, 1990, now abandoned.

BACKGROUND OF THE INVENTION

The present invention provides novel compounds, novel compositions, methods of their use and methods of their manufacture, such compounds being generally pharmacologically useful as anti-platelet aggregation agents in various vascular pathologies. The aforementioned pharmacologic activities are useful in the treatment of mammals. More specifically, the sulfonamide compounds of the present invention act by blocking the molecular receptor site of the protein fibrinogen. Fibrinogen is a glycoprotein that circulates in the blood plasma, and whose platelet receptor site is glycoprotein IIb/IIIa. By blocking the action of fibrinogen at the receptor (glycoprotein IIb/IIIa), the compounds of the present invention interfere with platelet aggregation, which is a cause of many vascular pathologies. At the present time, there is a need in the area of vascular therapeutics for such a fibrinogen receptor blocking agent. By interfering with hemostasis, such therapy would decrease the morbidity and mortality of thrombotic disease.

Hemostasis is the spontaneous process of stopping bleeding from damaged blood vessels. Precapillary vessels contract immediately when cut. Within seconds, thrombocytes, or blood platelets, are bound to the exposed matrix of the injured vessel by a process called platelet adhesion. Platelets also stick to each other in a phenomenon known as platelet aggregation to form a platelet plug. This platelet plug can stop bleeding quickly, but it must be reinforced by the protein fibrin for long-term effectiveness, until the blood vessel tear can be permanently repaired by growth of fibroblasts, which are specialized tissue repair cells.

An intravascular thrombus (clot) results from a pathological disturbance of hemostasis. The thrombus can grow to sufficient size to block off arterial blood vessels. Thrombi can also form in areas of stasis or slow blood flow in veins. Venous thrombi can easily detach portions of themselves called emboli that travel through the circulatory system and can result in blockade of other vessels, such as pulmonary arteries. Thus, arterial thrombi cause serious disease by local blockade, whereas venous thrombi do so primarily by distant blockade, or embolization. These diseases include venous thrombosis, thrombophlebitis, arterial embolism, coronary and cerebral arterial thrombosis and myocardial infarction, stroke, cerebral embolism, kidney embolisms and pulmonary embolisms.

There is a need in the area of cardiovascular and cerebrovascular therapeutics for an agent which can be used in the prevention and treatment of thrombi, with minimal side effects, including unwanted prolongation of bleeding in other parts of the circulation while preventing or treating target thrombi. The compounds of the present invention meet this need in the art by providing therapeutic agents for the prevention and treatment of thrombi.

The compounds of the present invention show efficacy as antithrombotic agents by virtue of their ability to block fibrinogen from acting at its platelet receptor site and thus prevent platelet aggregation.

SUMMARY OF THE INVENTION

The present invention relates to novel compounds having the general structural formula I:

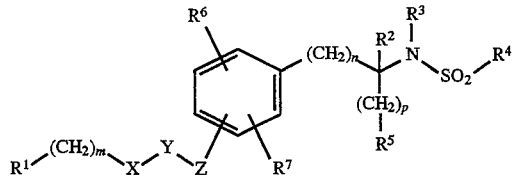

and the pharmaceutically aceptable salts thereof, wherein $R^1$ is, a four to eight member heterocyclic ring containing 1, 2, 3 or 4 heteroatoms wherein said hereto atoms are N, O or S and wherein said hetero ring is optionally substituted at any atom by H, $R^6$ or $R^7$;

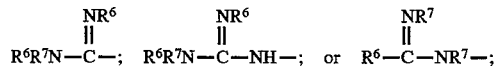

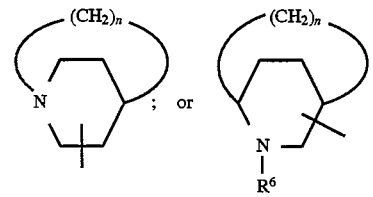

wherein $R^6$ and $R^7$ are independently hydrogen and unsubstituted or substituted $C_{0-10}$ alkyl and cycloalkyl wherein said substituents are $C_{1-10}$ alkoxy,
$C_{1-10}$ alkoxyalkyl,
$C_{1-10}$ alkoxyalkyloxy,
$C_{1-10}$ alkoxycarbonyl,
$C_{1-10}$ alkylcarbonyl,
$C_{4-10}$ aralkylcarhonyl,
$C_{1-10}$ alkylthiocarbonyl,
$C_{1-10}$ aralkylthiocarbonyl,
thiocarbonyl,
$C_{1-10}$ alkoxythiocarbonyl,
aryl,
a 5 to 6 membered saturated heterocyclic ring containing 1,2,3 or 4 hetero atoms wherein said heteroatoms are taken from the group consisting of N, O and S,
$C_{1-4}$ alkanoylamino,
$C_{1-6}$ alkoxycarbonyl-$C_{0-6}$ alkylamino,
$C_{1-10}$ alkylsulfonylamino,
$C_{4-10}$ aralkylsulfonylamino,
$C_{4-10}$ aralkyl,
$C_{1-10}$ alkaryl,
$C_{1-10}$ alkylthio,
$C_{4-10}$ aralkylthio,
$C_{1-10}$ alkylsulfinyl,
$C_{4-10}$ aralkylsulfinyl,
$C_{1-10}$ alkylsulfonyl,
$C_{4-10}$ aralkylsulfonyl,
aminosulfonyl,
$C_{1-10}$ alkylamtnosulfonyl,
$C_{4-10}$ aralkylsulfonylamino,
oxo, thio, unsubstituted and mono- and di-substituted 1-ethenyl, 2-ethenyl and 3-propenyl wherein said substituents are selected from the group consisting of hydrogen, $C_{1-10}$ alkyl and $C_{4-10}$ aralkyl, carboxy,
hydroxy,
amino,
$C_{1-6}$ alkylamino,
$C_{1-6}$ dialkylamino,
halogen, where halogen is defined as F, Cl, Br or I,
nitro, and
cyano, and further wherein said N can additionally be substituted to form a quaternary ammonium ion wherein said substituent is as previously defined for $R^6$ and $R^7$;

$R^2$ and $R^3$ are independently hydrogen, aryl and unsubstituted and substituted $C_{0-10}$ alkyl and cycloalkyl wherein said substituent is $C_{1-10}$ alkoxyalkyl, a 4 to 8 membered saturated heterocyclic ring system containing 1, 2, 3 or 4 heteroatoms, wherein said heteroatoms are taken from the group consisting of N, O and S, $C_{4-10}$ aralkyl,
$C_{1-10}$ alkaryl,
$C_{1-10}$ alkylthio,
$C_{4-10}$ aralkylthio,
$C_{1-10}$ alkylsulfinyl,
$C_{4-10}$ aralkylsulfinyl,
$C_{1-10}$ alkylsulfonyl,
$C_{4-10}$ aralkylsulfonyl,
carboxy,
$C_{1-10}$ alkylcarbonyl,
$C_{1-10}$ alkylthiocarbonyl,
$C_{4-10}$ aralkylcarbonyl,
$C_{4-10}$ aralkylthiocarbonyl,
$C_{1-6}$ alkoxycarbonyl,
$C_{4-10}$ aralkoxycarbonyl,
$C_{1-6}$ alkoxy,
$C_{1-6}$ alkoxycarbonyl-$C_{1-4}$ alkyl,
$C_{4-10}$ aralkoxycarbonyl-$C_{1-4}$ alkyl,
$C_{4-10}$ aralkoxy,
$C_{1-6}$ alkylamino,
$C_{1-12}$ dialkylamino,
$C_{1-6}$ alkanoylamino,
$C_{4-10}$ aralkanoylamino,
$C_{4-10}$ aralkylamino, $R^4$ is
aryl,
$C_{1-10}$ alkyl or cycloalkyl,
$C_{4-10}$ aralkyl,
$C_{1-10}$ alkoxyalkyl,
$C_{1-10}$ alkaryl,
$C_{1-10}$ alkylthioalkyl,
$C_{1-10}$ alkoxythioalkyl,
$C_{1-10}$ alkylamino,
$C_{4-10}$ aralkylamino,
$C_{1-10}$ alkanoylamino,
$C_{4-10}$ aralkanoylamino
$C_{1-10}$ alkanoyl, and
$C_{4-10}$ aralkanoyl, and unsubstituted or substituted $C_{1-10}$ carboxyalkyl wherein said substituent is aryl or $C_{1-10}$ aralkyl; further wherein any of the substituents for $R^4$ may be substituted by substituents selected from the group as defined for $R^6$;

$R^5$ is a four to eight member saturated or unsaturated heterocyclic ring containing 1, 2, 3 or 4 heterocyclic atoms wherein said heteroatoms are N, O and S and $$-\overset{\overset{O}{\|}}{C}-R^8, \quad -\overset{\overset{S}{\|}}{C}-R^8,$$

wherein $R^8$ is
hydroxy,
$C_{1-10}$ alkyloxy,
$C_{1-10}$ alkaryloxy,
$C_{4-10}$ aralkyloxy,
$C_{4-10}$ aralkylcarbonylory,
$C_{1-10}$ alkoxyalkyloxy,
$C_{1-10}$ alkoryalkylcarbonyloxy,
$C_{1-10}$ alkoxycarbonylalkyl,
$C_{1-10}$ alkylcarbonyloxyalkyloxy, an L- or D-amino acid joined by an amide linkage or an L- or D-amino acid joined by an amide linkage and wherein the carboxylic acid moiety of said amino acid is esterified by $C_{1-6}$ alkyl or $C_{4-10}$ aralkyl, $$-\overset{\overset{O}{\|}}{P}-OR^9, \quad -\overset{\overset{O}{\|}}{\underset{\underset{OR^{10}}{|}}{P}}-OR^9,$$

wherein $R^9$ and $R^{10}$ are selected from the group consisting of hydrogen, $C_{1-10}$ alkyl and $C_{4-10}$ aralkyl;

X and Y are independently $NR^6$, $(CH_2)_{0-3}$
O,
S, SO, $$-\overset{\overset{O}{\|}}{C}-; \quad -\overset{\overset{S}{\|}}{C}-; \quad -\overset{\overset{OH}{|}}{C}H-$$

$SO_2$,
$R^6R^7$
—C=C—,
—C≡C—, a 4- to 8-membered ring containing 0,1,2,3, or 4 heteroatoms chosen from N, O and S, wherein said ring is independently substituted at any atom with $R^6$, aryl, $$\overset{\overset{O}{\|}}{\underset{NR^6}{C}}$$

—$NR^6SO_2$—; —$SO_2NR^6$—; or $$\underset{NR^6}{\overset{\overset{O}{\|}}{C}}$$

Z is an optional substituent that, when present, is independently chosen as defined for X and Y;

m is an integer of from zero to ten;

n is an integer of from zero to ten; and p is an integer of from zero to three.

A preferred group of compounds of the present invention are those defined for general structural formula II as:

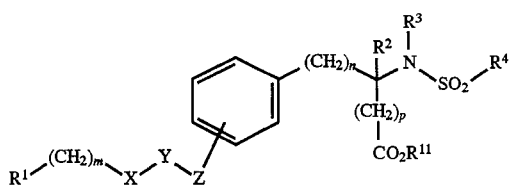

wherein

R[1] is a five to six member heterocyclic ring wherein said heteroatoms are N, O or S and wherein said heterocyclic ring is optionally substituted by $C_{1-5}$ alkyl; or $NR^6R^7$ wherein $R^6$ and $R^7$ are independently hydrogen, unsubstituted or substituted $C_{1-10}$ alkyl wherein said substituent is $C_{1-10}$ alkoxycarbonyl, aryl, $C_{0-5}$ dialkylamino-$C_{1-10}$ alkyl, $C_{4-10}$ aralkyl, and further wherein said N can additionally be substituted to form a quaternary ammonium ion wherein said substituent is as previously defined for $R^6$ and $R^7$;

$R^2$ and $R^3$ are hydrogen and $C_{1-4}$ alkyl, $C_{4-10}$ aralkyl;

$R^4$ is aryl, $C_{1-10}$ alkyl or cycloalkyl, $C_{4-10}$ aralkyl, $C_{1-10}$ alkoxyalkyl, $C_{1-10}$ alkaryl, unsubstituted or substituted $C_{1-10}$ carboxyalkyl wherein said substituent is aryl, $C_{1-6}$ alkyl, or $C_{4-10}$ aralkyl;

$R^{11}$ is hydrogen or $C_{1-10}$ alkyl;

X and Y are independently aryl, O, $SO_2$, $(CH_2)_{0-3}$ —CH=CH—;

$SO_2NR^6$—; or —$NR^6SO_2$ a 5 or 6-membered ring containing 0,1 or 2 heteroatoms chosen from N or O;

Z is an optional substituent that, when present, is O, $SO_2$, —$NR^6CO$—, —$CONR^6$—, $C_{1-10}$ straight or branched alkyl;

m is an integer of from zero to eight;

n is an integer of from zero to two; and p is an integer of from zero to two.

A more preferred group of compounds of the present invention are those defined for general structure formula III as

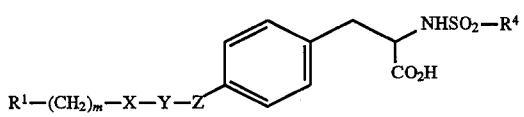

wherein

R[1] is a five or six membered heterocyclic ring wherein said heteroatoms are N and O and wherein said heterocyclic ring is optionally substituted by $C_{1-5}$ alkyl;

$NR^6R^7$ wherein $R^6$ and $R^7$ are independently $C_{1-10}$ alkyl, or $C_{4-10}$ aralkyl and further wherein said N can additionally be substituted to form a quaternary ammonium ion wherein said stubstituent is as previously defined for $R^6$ and $R^7$;

$R^4$ is aryl, $C_{1-10}$ alkyl or cycloalkyl, or $C_{4-10}$ aralkyl;

X and Y are independently phenyl O, $SO_2$, $(CH_2)_{0-3}$

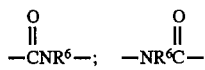

or a 5- or 6- membered ring containing 0 or 1 heteroatoms chosen from N or O;

Z is an optional substitutent that, when present, is O, $SO_2$, —$NR^6CO$—, —$CONR^6$—, or —$CH_2$—; and m is an integer of from zero to six.

Preferred compounds of the present invention are:

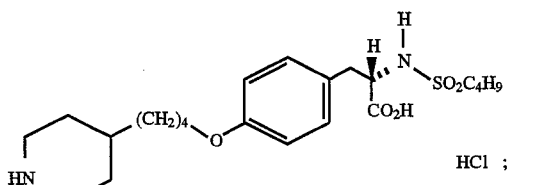

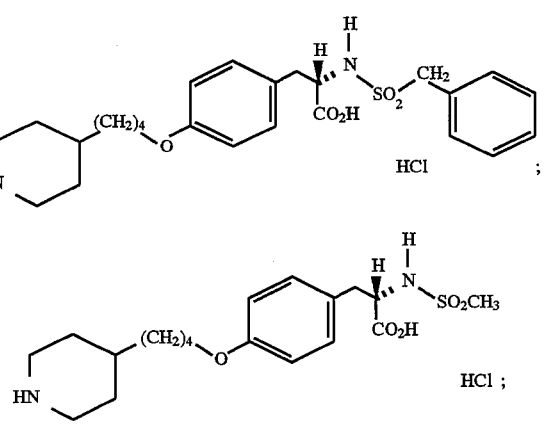

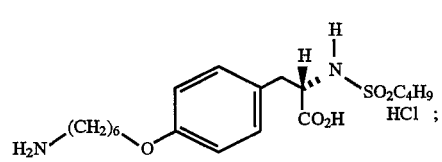

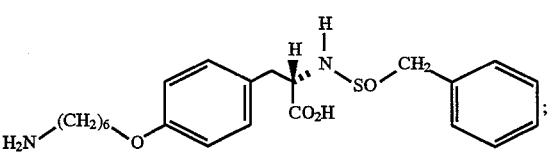

and

2-S-(2-Styrylsulfonylamino)-3-[4-(piperidin-4-ylbutyloxyphenyl]-propionic acid hydrochloride;

2-S-(Phenylsulfonylamino)-3-[4-(piperidin-4-yl) butyloxyphenyl]-propionic acid hydrochloride;

2-S-(2-Phenethylsulfonylamino)-3-[4-(piperidin-4-yl) butyloxyphenyl]-propionic acid hydrochloride;

2-S-(2-Thienylsulfonylamino)-3-[4-(piperidin-4-yl) butyloxyphenyl]-propionic acid hydrochloride;

2-S-(Dansylamino)-3-[4-(piperidin-4-yl)-butyloxyphenyl] propionic acid hydrochloride;

2-S-(Butylsulfonylamino)-3-[4-(piperidin-4-yl) oxyphenyloxy]-phenylpropionic acid hydrochloride;

2-S-(Butylsulfonylamino)-3-[4-(6-amino-hexyloxy)phenyl] propionic acid hydrochloride;

2-S-(Butylsulfonylamino)-3-[4-(piperidin-4-yl)-2,2-dimethyl]-butyloxyphenylpropionic acid;

3-S-(Butylsulfonylamino)-4-[4-piperidin-4-yl) butyloxyphenyl]butanoic acid;

2-S-(Methylsulfonylamino)-3-[4-(6-aminohexyloxy) phenyl]-propionic acid;

2-S-(Butylsulfonylamino)-3-[4-(6-aminohexyloxy)phenyl]-propionic acid;

{2-[4-[4-Pipezidin-4-yl)butyloxyphenyl]-1-n-butylsulfonylamino)}-ethane-phosphonic acid and ethyl ester;

{2-[4-[4-Piperidin-4-yl)butyloxyphenyl]-1-n-butylsulfonylamino)}-ethane-phosphonic acid; and
Ethyl-2-S-Benzylsulfonylamino-3-[4-(piperidin-4-yl)butyloxyphenyl]-propionate.

DETAILED DESCRIPTION OF THE INVENTION

The term "pharmaceutically acceptable salts" shall mean non-toxic salts of the compounds of this invention which are generally prepared by reacting the free base with a suitable organic or inorganic acid. Representative salts include the following salts:

Acetate
Benzenesulfonate
Benzoate
Bicarbonate
Bisulfate
Bitartrate
Borate
Bromide
Calcium Edetate
Camsylate
Carbonate
Chloride
Clavulanate
Citrate
Dihydrochloride
Edetate
Edisylate
Estolate
Esylate
Fumarate
Gluceptate
Gluconate
Glutamate
Glycollylarsanilate
Hexylresorcinate
Hydrabamine
Hydrobromide
Hydrochloride
Hydroxynaphthoate
Iodide
Isothionate
Lactate
Lactobionate
Laurate
Malate
Maleate
Mandelate
Mesylate
Methylbromide
Methylnitrate
Methylsulfate
Mucate
Napsylate
Nitrate
Oleate
Oxalate
Pamaote
Palmitate
Pantothenate
Phosphate/diphosphate
Polygalacturonate
Salicylate
Stearate
Subacetate
Succinate
Tannate
Tartrate
Teoclate
Tosylate
Triethiodide
Valerate The term "pharmacologically effective amount" shall mean that amount of a drug or pharmaceutical agent that will elicit the biological or medical reponse of a tissue, system or animal that is being sought by a researcher or clinician. The term "anti-coagulant agent" shall include aspirin, heparin and warfarin. The term "fibrinolytic agent" shall include streptokinase and tissue plasminogen activator.

The term "aryl" shall mean a mono- or polycylic ring system composed of 5- and 6-membered aromatic rings containing 0, 1, 2, 3, or 4 heteroatoms chosen from N, O, and S and either unsubstituted or substituted with $R^6$.

The term "alkyl" shall mean straight or branched chain alkane, alkene or alkyne.

The term "alkoxy" shall be taken to include an alkyl portion where alkyl is as defined above.

The terms "aralkyl" and "alkaryl" shall be taken to include an alkyl portion where alkyl is as defined above and to include an aryl portion where aryl is as defined above.

The term "halogen" shall include fluorine, chlorine, iodine and bromine.

The term "oxo" shall mean the radical =O.

The term "thio" shall mean the radical =S.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardivascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardivascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et. al., Amer. J. Physiol., 1987, 252:H, pp 615–621). Platelets released from artificial surfaces show impaired hemostatic function. Compounds of the invention may be administered to prevent adhesion.

Other application of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures. They may also be used to prevent mycocardial infarction.

The compounds of the present invention can be administered in such oral dosage forms as tablets, capsules, pills, powders, granules, elixers, tinctures, suspensions, syrups and emulsions. Likewise, they may also be administered in intravenous, intraperitoneal, subcutaneous or intramuscular form, all using forms well known to those of ordinary skill in the pharmaceutical arts. An effective but non-toxic mount of the compound desired can be employed as an antiaggregation agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day and preferably 1.0–100 mg/kg/day and most preferably 1.0 to 50 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesuim stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonits, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy burytic acid, polyorthoesters, polyacetals, polydihydropyrans, polycyanoacrylates and cross-linked or amphipathic block copolymers of hydrogels.

The compounds of the present invention can also be co-administered with suitable anti-coagulant agents or thrombolytic agents to achieve synergistic effects in the treatment of various vascular pathologies.

The compounds of formula I can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to he construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative precedures can be used to prepare these compounds. All temperatures are degrees Celsius unless noted otherwise.

Reagent symbols have the following meanings:
BOC: t-butyloxycarbonyl
Pd-C: Palladium on activated carbon catalyst
DMF: Dimethylformamide
DMSO: Dimethylsulfoxide
CBZ: Carbobenzyloxy
$CH_2Cl_2$: Methylene chloride
$CHCl_3$: Chloroform
EtOH: Ethanol
MeOH: Methanol
EtOAc: Ethyl acetate
HOAc: Acetic acid
THF: Tetrahydrofuran Generally, compounds of the invention are prepared as follows:

Scheme 1

A suitably N-protected (BOC or CBZ) tyrosine is O-alkylated by treatment with a base, such as NaH or KH, followed by an alkylating agent.* This reaction is typically carried out in DMF or ether (THF) solvents at 0°–40° for from 1–12 hours. The product is esterified, eg. methyl or ethyl ester, with $Cs_2CO_3$/MeI (or EtI) in a polar, aprotic solvent such as DMF and then hydrogenated in the presence of a catalyst such as Pd/C to remove the N-protecting group. Sulfonylation of the amino ester is effected by treatment of a sulfonyl halide, such as a chloride, in an organic solvent, such as EtOAc, THF, or $CH_3CN$, in the presence of an inorganic base, such as $NaHCO_3$ or $KHCO_3$ or an organic base such as pyridine or triethylamine. Final deprotection is then carried out by hydrolysis in base, LiOH or NaOH in homogeneous solution of THF, $CH_3OH/H_2O$, followed by acid treatment with HCl gas or $CF_3CO_2H/CH_2Cl_2$.

*This alkylating agent typically is a halide such as a Bromide, iodide, or chloride, but may involve other leaving groups such as tosylate. This alkylating agent may also contain a protected amino site within the molecule, such as an N-BOC or N-CBZ moiety, and may be cyclic, acyclic, benzylic or allylic.

Scheme 3

Analogs of tyrosine may be used in similar sequences to that described above. The 4-hydroxyphenylated tyrosine 3-2 is protected on the free amino group with CBZ or similar appropriate reagent and then alkylated on the phenolic oxygen. This former reaction is typically carried out in water/dioxane solution at 0°–10° in the presence of an inorganic base, such as $Na_2CO_3$ or $K_2CO_3$, by treatment of the phenol with an acid chloride as benzyl chloroformate or similar aryl or alkyl chloroformate. Phenolic oxygen alkylation is typically carried out in a hydrocarbon solvent, such as benzene or toluene, in the presence of $Ph_3P$, or similar aryl or alkylphosphine, and the appropriate alkanol, such as N-BOC-piperidin-4-ol. Removal of the N-protecting group by catalytic hydrogenation in the case of N-CBZ and sulfonylation of the free amine gives the advanced intermediate. Sulfonylation is typically carried out in EtOAc solution, halocarbon solvents such as $CH_2Cl_2$ are also appropriate, at 0°–25° for 1–10 hours in the presence of an inorganic base, such as $Na_2CO_3$ or $K_2CO_3$ or organic bases such as pyzidine and N-methylmorpholine. Final depzotection with base/ LiOH or NaOH in THF/alkanol/$H_2O$) followed by acid (HCl gas/EtOAc or $CF_3CO_2H/CH_2Cl_2$) provides the final product.

Scheme 4

Modification of the alkylating agent for the tyrosine O allows a variety of amino terminal groups to be used. For example, N-CBZ esters, such as 4-1 can be treated with alkyl organometallic reagents such as methyl lithium or ethyl magnesium bromide to provide substituted alcohols such as 4-2.* Alkylation of phenol as described above in Scheme 3 and analogous structural modification afford diverse final products.

*These esters may be aliphatic or aromatic and may possess suitably protected N-functionality as in linear or cyclic amines.

Scheme 5

Novel chain extension at the C-terminus is effected by conversion of the N-protected carboxylic acid of tyrosine to an α-diazo ketone. This conversion typically involves treatment of the acid anhydride or acid chloride with diazomethane, followed by rearrangement under thermal conditions or in the presence of a catalyst such as silver benzoate in an alkanol solvent at 0°–40° for from 1–10 hours. The resulting methylene extended ester may then be N-deprotected at the α-amino site, and converted to final products as described above. Typically, the free α-amino group is acylated or sulfonylated as described above to provide a suitable advanced intermediate. This is then deprotected under conditions that remove the carboxy and amino protecting groups to give final products.

The source for the following compounds is as shown:

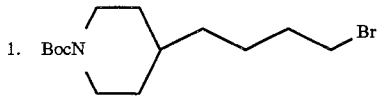

is described below.

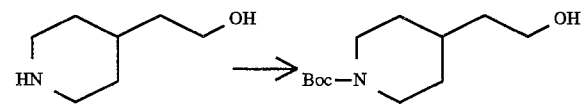

2-(4-N-t-Butyloxycarbonylpiperidinyl)ethanol

4-Piperidine-2-ethanol (Available from Aldrich) (130 g, 1.0 mole) was dissolved in 700 mL dioxane, cooled to 0° C. and treated with 3N NaOH (336 mL, 1.0 mole), and di-t-butylcarbonate (221.8 g, 1.0 mole). The ice Bath was removed and the reaction stirred overnight. The reaction was concentrated, diluted with water and extracted with ether. The ether layers were combined, washed with brine, dried over $MgSO_4$, filtered and evaporated to give 225.8 g of product (98%).

$R_f$=0.37 in 1:1 EtOAc/Hexanes, ninhydrin stain $^1$H NMR (300 MHz, $CDCl_3$) δ 4.07 (bs, 2H), 3.7 (bs, 2H), 2.7 (t, J=12.5 Hz, 2H), 1.8–1.6 (m, 6H), 1.51 (s, 9H), 1.1 (ddd, J=4.3, 12.5, 12 Hz, 2H).

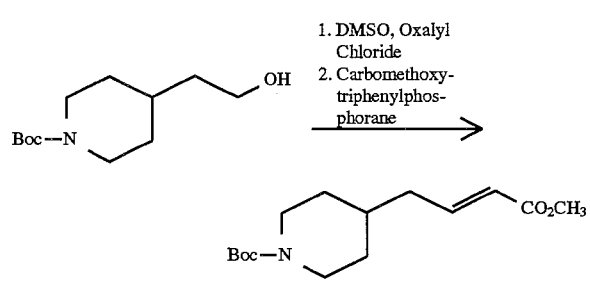

Methyl 4-(4-N-t-butyloxycarbonylpiperidinyl)-but-2-enoate

Oxalyl chloride (55.8 mL, 0.64 mole) was dissolved in 1L $CH_2Cl_2$ and cooled to −78° C. under $N_2$. DMSO (54.2 mL, 0.76 mole) was added dropwise. After gas evolution had ceased, 2-(4-N-t-butyloxy-carbonylpiperidinyl)ethanol (102.5 g, 0.45 mole) dissolved in 200 mL $CH_2Cl_2$ was added over 20 minutes. After stirring an additional 20 minutes, triethylamine (213 mL, 1.53 mole) was added dropwise and the cold bath removed. After 1 and ½ hours TLC showed starting material gone. Carbomethoxytriphenylphosphorane (179 g, 0.536 mole) was added and the reaction stirred overnight. The solution was diluted with 300 mL $Et_2O$, extracted once with 800 mL $H_2O$, twice with 300 mL 10% $KHSO_4$ solution, then once with 300 mL brine. The organic layer was dried over $MgSO_4$, filtered and evaporated. Column chromatography ($SiO_2$, 5% EtOAc/Hexanes) yielded 78.4 g (62%) of pure methyl 4-(4-N-t-butyloxycazbonylpiperidinyl) but-2-enoate. $^1$H NMR (300 MHz, $CDCl_3$) δ 6.9 (ddd J=15.6, 7.6, 7.6 Hz, 1H), 5.8 (d, J=15.6 Hz, 1H), 4.0 (bs, 2H), 3.7 (s, 3H), 2.6 (t, J=12.6 Hz, 2H), 2.1 (t, J=7.4 Hz, 2H), 1.7–1.4 (m, 3H), 1.4 (s, 9H), 1.1 (m, 2H).

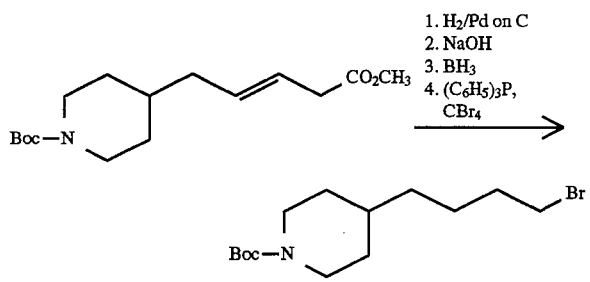

4-(4-N-t-Butyloxycarbonylpiperidinyl)butyl bromide

Methyl 4-(4-N-t-butyloxycarbonylpipezidinyl)but-2-enoate (36.2 g, 0.128 mole), was dissolved in 500 mL EtOAc. 10% Palladium on carbon (10 g) was added as a slurry in EtOAc and the reaction was placed under $H_2$ (in a balloon) overnight. The reaction was filtered through Solka-Floc, the cake washed with EtOAc and the ethyl acetate evaporated to give 34.7 g (90%) of methyl 4-(4-N-t-butyloxycarbonylpiperidin-4-yl)butanoate. TLC $R_f$=0.69 in 30% EtOAc/Hexanes.

$^1$H NMR (300 MHz, CDCl$_3$) δ 4.0 (bs, 2H), 3.6 (s, 3H), 2.60 (t, J=12.3 Hz, 2H), 2.20 (t, J=7.4, 2H), 1.6 (m, 4H), 1.40 (s, 9H), 1.40 (m, 1H), 1.20 (m, 2H), 1.0 (m, 2H).

The butanoate ester (45.3 g, 0.159 mole) was dissolved in CH$_3$OH and treated with 1N NaOH (500 mL, 0.5 mole) overnight. The solvent was removed in vacuo, water was added and the solution washed with ether, then acidified with 10% KHSO$_4$ solution. The aqueous layer was washed with ether, the ether layers were combined, washed with brine, dried (MgSO$_4$), and concentrated to give the corresponding acid as a clear oil (41.85 g, 97% yield).

$^1$H NMR (300 MHz, CDCl$_3$) δ 4.0 (bs, 2H), 2.6 (m, 2H), 2.25 (m, 2H), 1.6 (bs, 4H, 1.4 (s, 9H), 1.3–0.9 (9H).

This acid (20.4 g, 0.077 mole) was treated with borane (BH$_3$/THF, 235 mL, 235 mmole) in THF at 0° for 1 hour. NaOH (1N, 250 mL) was added dropwise and the solution stirred overnight. The resulting reaction mixture was concentrated to remove THF and extracted with ether. The ether extracts were combined, dried over MgSO$_4$, filtered and evaporated to give the corresponding alcohol as 19.7 g of a colorless oil.

$R_f$=0.7 in 2:1 ethyl acetate/hexanes.

$^1$H NMR (300 MHz, CDCl$_3$) δ 4.1 (bs, 2H), 3.6 (t, 2H), 2.65 (t, 2H), 2.1 (bs, 1H), 1.65 (bs, 2H), 1.55 (m, 2H), 1.4 (s, 9H), 1.35 (m, 3H), 1.25 (m, 2H), 1.1 (m, 2H).

This alcohol (19.7 g, 76.5 mmole) was dissolved in THF and treated with triphenylphosphine (23.1 g, 88 mmole) and cooled to 0° C. Carbon tetrabromide (29.8 g, 89.9.mmol) was added in one portion, the cold hath was removed and the reaction stirred overnight. Additional triphenyl phosphine (11.71 g) and carbon tetrabromide (14.9 g) was added to drive the reaction to completion. The mixture was filtered and the liquid was diluted with ether and filtered again. After solvent removal the resulting liquid was adsorbed onto SiO$_2$ and chromatographed with 5% EtOAc/Hexanes to yield 4-(4-N-t-butyloxy-carbonylpiperidin-4-yl)butyl bromide as a clear colorless oil (20.7 g, 85% yield).

$R_f$=0.6 in 1:4 ethyl acetate/hexanes $^1$H NMR (300 MHz, CDCl$_3$) δ 4.1 (bs, 2H), 3.4 (t, 2H), 2.65 (t, 2H), 1.85 (m, 2H), 1.65 (bd, 2H), 1.4 (s, 9H), 1.35 (m, 2H), 1.3 (m, 3H), 1.1 (m, 2H).

2.BocNH(CH$_2$)$_6$Br Commercial H$_2$N(CH$_2$)$_5$CH$_2$OH was protected as the N-Boc derivative in standard fashion and this was converted to the bromide with Ph$_3$P/CBr$_4$ in THF. Utilization of starting amino alcohols of varying chain lengths provides the analogous halides in this manner.

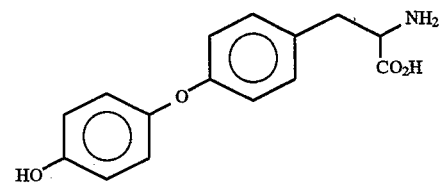

Purchased from Sigma.

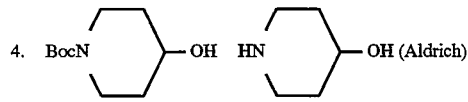

was N-Boc protected in the standard manner.

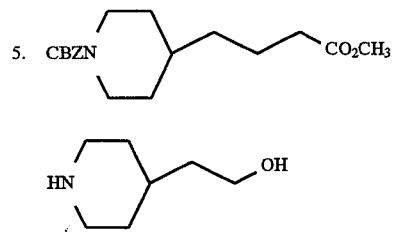

was N-Cbz protected in the standard fashion and converted to final product as described in U.S. Ser. No. 589,145.

SCHEME 1

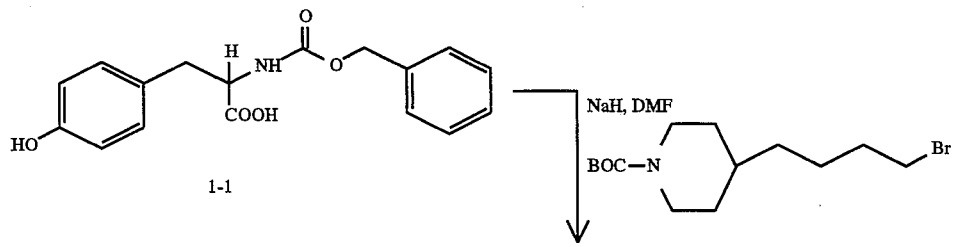

-continued
SCHEME 1
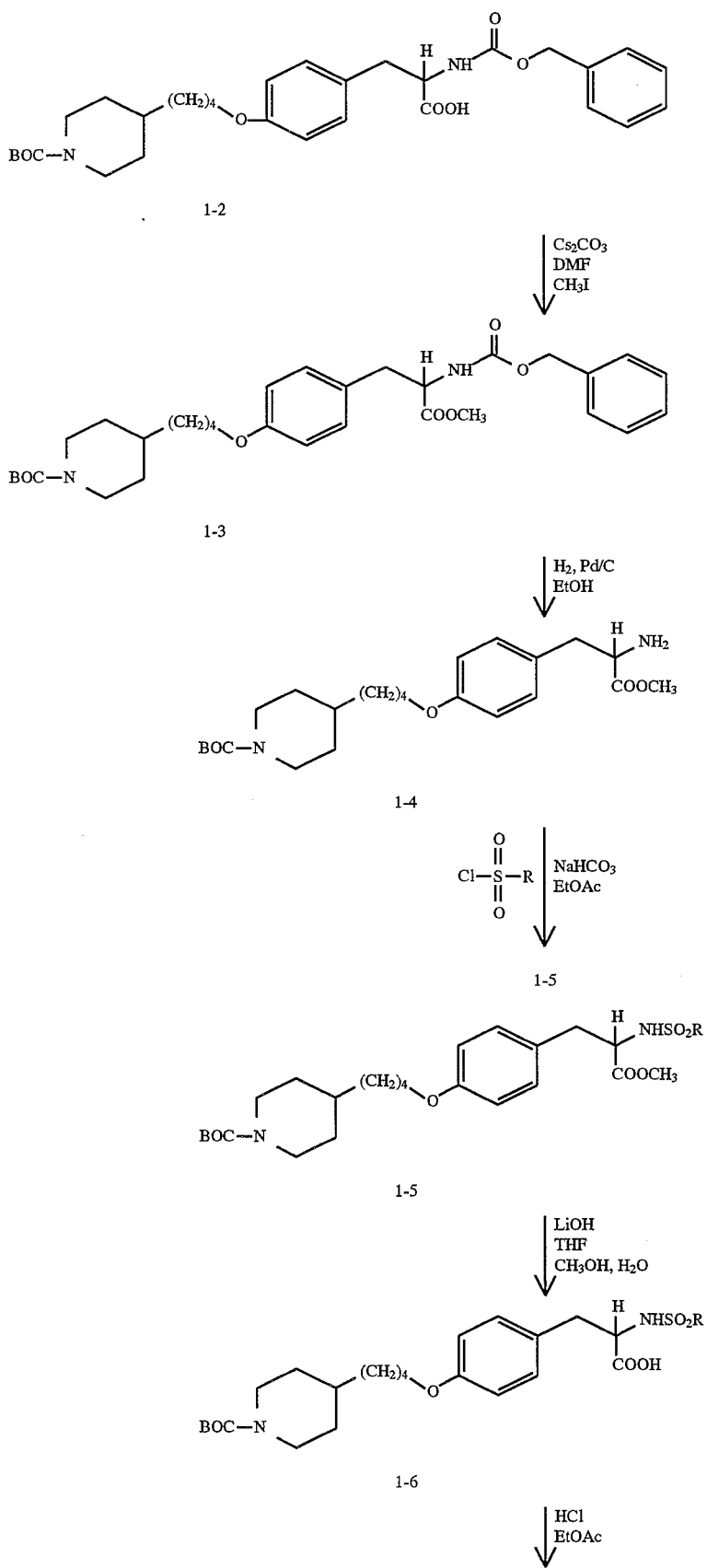

-continued
SCHEME 1

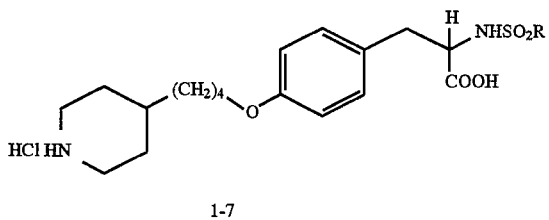

1-7

EXAMPLE 1

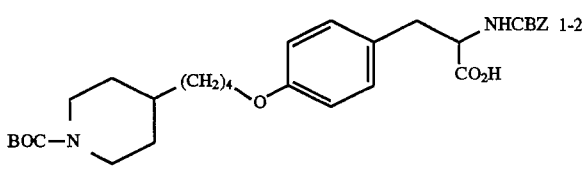

2-S-(Benzyloxycarbonylamino)-3-[4-(N-t-butyloxycarbonylpiperidin-4-yl)butyloxyphenyl] propionic acid (1-2)

N-CBZ-L-tyrosine (1-1) (17.58 g, 0.055 mmole) was dissolved in DMF (75 mL), cooled to 0°–10° C. and treated with sodium hydride (2.88 g, 0.12 mole). This suspension was stirred at 0°–10° C. for 1 hour and then N-t-butyloxycarbonylpiperidin-4-ylbutyl bromide (17.70 g, 0.055 mole) in 25 mL DMF was added dropwise over 15 minutes. The reaction mixture was then stirred at room temperature for 16 hours. The solvent was removed in vacuo and the residue was taken up in a mixture of 500 mL EtOAc/100 mL 10% KHSO$_4$. The organic phase was washed with brine, dried (Na$_2$SO$_4$) and the solvent was removed to give a viscous oil. This was purified by flash chromatography on silica gel eluting with 98:2:0.5 CHCl$_3$/CH$_3$OH/HOAc to give pure 1-2 (23.75 g), R$_f$=0.35, as a pale yellow oil.

$^1$H NMR (300 MHz, CDCl$_3$) δ 1.00–1.15 (2H, m), 1.20–1.80 (16H, m), 2.62 (2H, t), 3.10 (2H, m), 3.91 (2H, t), 4.04 (2H, m), 5.10 (2H, m), 5.22 (1H, d), 6.78 (2, d), 7.04 (2H, d), 7.35 (5H, m).

EXAMPLE 2

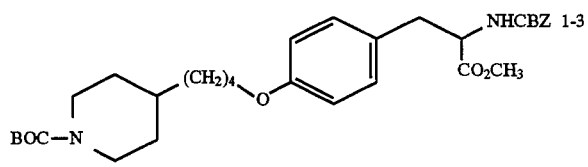

Methyl 2-S-(Benzyloxycarbonylamino)-3-[4-(N-t-butyloxycarbonylpiperidin-4-yl)butyloxyphenyl]-propionic acid (1-3)

1-2 (10.05 g, 18.1 mmole) was dissolved in CH$_3$OH (150 mL) at room temperature and cesium carbonate (2.95 g, 9.06 mmole) was added and the resulting mixture stirred for 15 minutes to give a clear solution. The CH$_3$OH was removed at reduced pressure and the residue was then dissolved in DMF (150 mL) and treated dropwise with methyl iodide (2.57), 18.1 mmole). The resulting solution was stirred overnight at room temperature. The solvent was removed in vacuo and the residue was taken up in 400 mL ether and washed with 3×50 mL portions of H$_2$O, 50 mL brine and dried (Na$_2$SO$_4$). Solvent removal provided 1-3 as an oil.

$^1$H NMR (300 MHz, CDCl$_3$) δ 1.0–1.15 (2H, m), 1.30–1.70 (16H, m), 2.68 (2H, dt), 3.05 (2H, m), 3.72 (3H, s), 3.91 (2H, t), 4.08 (2H, d), 4.61 (1H, m), 5.10 (2H, m), 5.18 (1H, m), 6.79 (2H, d), 6.98 (2H, d), 7.35 (5H, m).

EXAMPLE 3

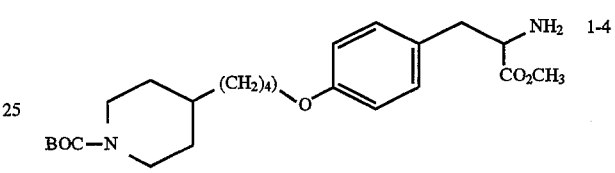

Methyl 2-S-Amino-3-[4-(N-t-butyloxycarbonylpiperidin-4-yl)-butyloxyphenyl] propionate (1-4)

To 1-3 (5.0 g, 8.79 mmole) dissolved in absolute ethanol (150 mL) was added 10% Pd/C (0.5 g) and the resulting suspension was hydrogenated under balloon pressure for 12 hours. The catalyst was then filtered off and the solvent was removed in vacuo to give 1-4 (3.6 g) as an oil.

$^1$H NMR (300 MHz, CDCl$_3$) δ 1.00–1.20 (2H, m), 1.22–1.55 (12H, m), 1.60–1.75 (4H, m), 2.00 (2H, bs), 2.68 (2H, t), 2.87 (1H, dd), 3.05 (1H, dd), 3.72 (3H, s), 3.93 (2H, t), 4.09 (2H, m), 6.82 (2H, d), 7.10 (2H, d).

EXAMPLE 4

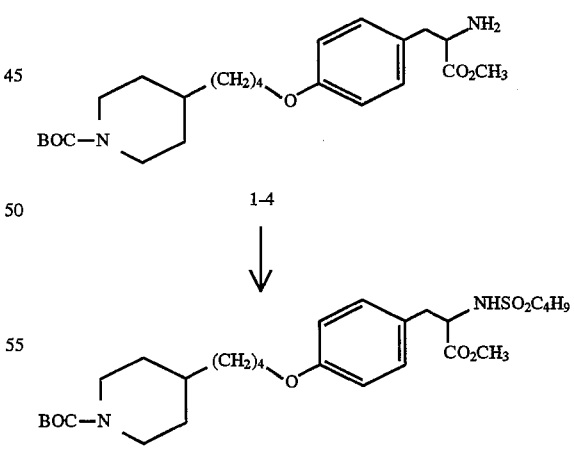

Methyl 2-S-(n-Butylsulfonylamino)-3-[4-(N-t-butyloxycarbonylpiperidin-4-yl)butyloxyphenyl]-propionate (1-8)

1-4 (0.59 g, 1.36 mmole) was dissolved in ethyl acetate (10 mL) and NaHCO$_3$ (0.7 g, 8.68 mmole) was added with stirring at room temperature followed by butanesulfonyl chloride (0.36 mL, 2.76 mole) and the resulting mixture was refluxed for 26 hours. The cooled reaction mixture was filtered and concentrated and the residue was purified by flash chromatography on silica gel eluting with 4:1 hexane/ EtOAc to give pure 1-8 (0.305 g) R$_f$=0.7 in 1:1 hexane/ EtOAc, ninhydrin stain.

$^1$H NMR (300 MHz, CDCl$_3$) δ 0.82 (3H, t), 1.05 (2H, ddd), 1.45 (9H, s), 1.1–1.6 (1H, m), 1.7 ( 4H, m), 2.6 (2H, t), 2.6–2.8 (2H, m), 2.78 (1H, dd), 3.05 (1H, dd), 3.7 (3H, s), 3.93 (2H, t), 4.05 (2H, bd), 4.15 (1H, dd), 6.85 (2H, d), 7.15 (2H,d).

EXAMPLE 5

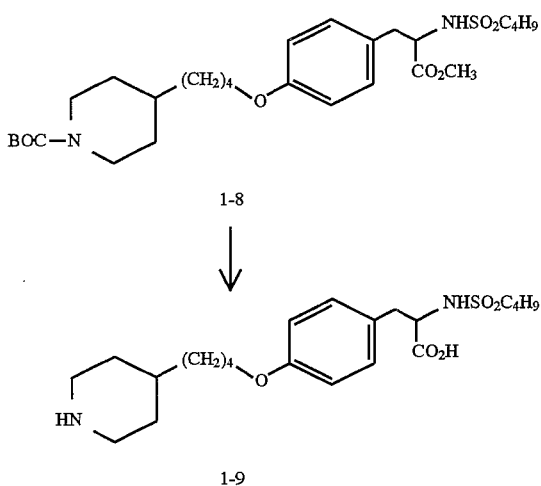

2-S-(n-Butylsulfonylamino)-3[4-(piperidin-4-yl) butyloxyphenyl]propionic acid hydrochloride (1-9)

1-8 (0.325 g, 0.59 mmole) was dissolved in 1:1:1 CH$_3$OH/ H$_2$O/THF and LiOH•H$_2$O (0.157 g, 3.76 mmole) was added. The resulting solution was stirred at room temperature for 3 hours, then concentrated, diluted with 10% KHSO$_4$ and extracted with EtOAc. This provided 2-S-(n-butylsulfonylamino)-3[4-(N-t-butyloxycarbonylpiperidin-4-yl)butyloxyphenyl]-propionic acid. This acid (0.315 g, 0.59 mmole) was dissolved in EtOAc (20 mL) and treated with HCl gas at −20° C. for 15 minutes. The reaction mixture was then stoppered and was stirred at −5° C. for 1 hour at which time all starting material was consumed. Argon gas was bubbled through the reaction mixture for 15 minutes and the solvent was removed to give a residue that was triturated with ether to provide pure 1-9 (0.29 g) as a pale yellow solid.

$^1$H NMR (300 MHz, CD$_3$OD) δ 0.85 (3H, t), 1.2 (2H, dd), 1.2–1.7 (9H, m), 1.7 (2H, m), 1.95 (2H, bs), 2.65 (2H, t), 2.8 (1H, dd), 2.95 (2H, bt), 3.10 (1H, dd), 3.83 (2H, bs), 3.95 (2H, t), 4.1 (1H, dd), 6.85 (2H, d), 7.2 (2H, d).

Analysis for C$_{22}$H$_{36}$N$_2$O$_5$1S•HCl•0.8 H$_2$O Calculated: C=53.76, H=7.92, N=5.70 Found: C=53.76, H=7.66, N=5.44.

EXAMPLE 6

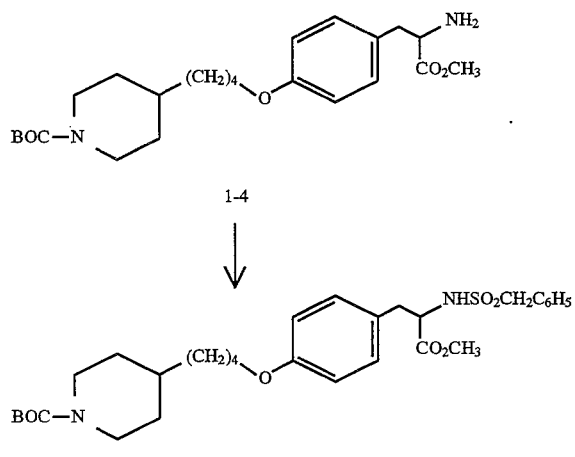

Methyl 2-S-(Benzylsulfonylamino)-3-[4-(N-t-butyloxy-carbonylpipezidin-4-yl)butyloxyphenyl] propionate (1-10)

1-4 (0.59g, 1.36 mmole) was treated with benzylsulfonyl chloride (0.263 g, 1.38 mmole) as described above for 1-8. The crude reaction product was purified by flash chromatography on silica gel eluting with 3:1 hexane/EtOAc to give pure 1-10 (0.35 g) as an oil.

$^1$NMR (300 MHz, CD$_3$OD) δ 0.85–1.10 (2H, m), 1.10–1.23 (2H, m), 1.35–1.52 (11H, m), 1.61–1.80 (4H, m), 2.65–3.00 (4H, m), 3.65 (3], s), 3.90–4.14 (5H, m), 6.85 (2H, d), 7.08 (2H, d), 7.22 (2H, m), 7.30 (3H, m).

EXAMPLE 7

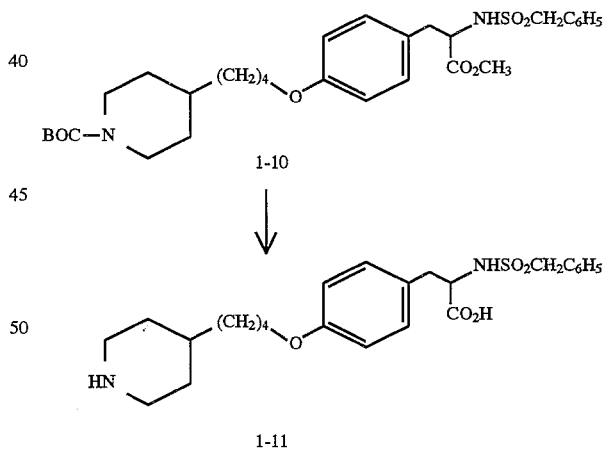

2-S-(Benzylsulfonylamino)-3-[4-(piperidin-4-yl) butyl-oxyphenyl]propionic acid hydrochloride (1-11)

Treatment of 1-10 (0.354 g, 0.60 mole) with LiOH (0.15 g, 3.7 mmole) as described for 1-8 gave 2-S-(benzylsulfonylamino)-3-[4-(N-t-butyloxycarhonylpiperidin-4-yl)butyloxyphenyl]propionic acid (0.35 g) as a viscous oil.

$^1$H NMR (300 MHz CD$_3$OD) δ 0.84–1.06 (3H, m), 1.23 (4H, m), 1.34–1.50 (11H, m), 1.60–1.78 (5H, m), 2.65 (2H, bt), 2.82 (1H, m), 3.02 (1H, m), 3.91 (2H, m), 3.96–4.12 (5H, m), 6.83 (2H, d), 7.15 (2H, d), 7.22 (2H, m), 7.29 (3H, m).

This acid (0.35 g, 0.60 mmole) was dissolved in 20 mL EtOAc and treated with HCl gas as described for 1-9 to give pure 1-11 as a white solid (0.30 g).

$^1$H NMR (300 MHz, CD$_3$OD) δ 1.32 (4H, m), 1.40–1.65 (3H, m), 1.72 (2H, m), 1.92 (2H, d), 2.77–3.08 (4H, m), 3.33 (3H, m), 3.95–4.14 (5H, m), 6.86 (2H, d), 7.17 (2H, d), 7.28 (2H, m), 7.31 (3H, m).

3.62 (3H, s), 3.88 (2H, t), 4.09 (2H, m), 4.22 (1H, m), 4.98 (1H, d), 6.45 (1H, d), 6.80 (2H, d), 7.06 (2H, d), 7.40 (4H, s).

2-S-(2-Styrylsulfonylamino)-3-[4-(piperidin-4-yl)butyloxyphenyl)propionic acid hydrochloride (1-13)

1-12 (0.58 g, 0.97 mmole) was dissolved in THF(1)-H$_2$O(1)-MeOH(1) (15 ml) and lithium hydroxide (0.12 g, 5.0 mmole) was added and the resulting clear solution was stirred overnight at room temperature.

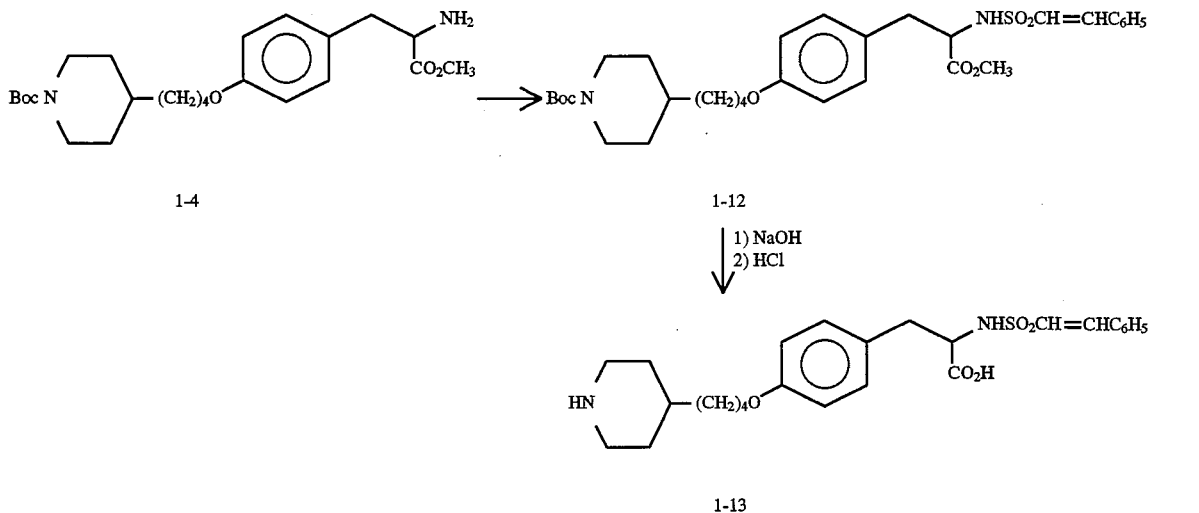

Methyl 2-S-(2-Styrylsulfonylamino)-3-[4-(N-t-butyloxycarbonylpiperidin-4-yl)butyloxyphenyl]propionate (1-12)

1-4 (0.647 g, 15 mmoles) was dissolved in ethyl acetate (20 ml), and NaHCO$_3$ (0.454 g, 5.4 mmoles) was added followed by β-styrenesulfonyl chloride (0.365 g, 18.0 moles) and the resulting reaction mixture was heated at reflux with stirring for 16 hours. The cooled reaction mixture was filtered, the solvent removed and the residue was purified by flash chromatography on silica gel eluting with hexane (3)/ethyl acetate (1) to give pure 1-12.

$^1$H NMR (300 MHz, CDCl$_3$) δ 1.10 (2H, m), 1.30–1.55 (14 H, m), 1.65–1.80 (4H, m), 2.68 (2H, t), 3.01 (2H, dt),

The reaction mixture was diluted with 75 ml H$_2$O, acidified to pH 2-3 with 10% KHSO$_4$ solution and then extracted with 3×50 ml EtOAc. The organic extract was dried, the solvent removed, and the residue purified by flash chromatography on silica gel eluting with CHCl$_3$(97)-MeOH(3)-HOAc(1) to give the desired acid (R$_f$=0.2).

This acid was dissolved in EtOAc and treated with HCl gas as described for 1-9 to give 1-13.

$^1$H NMR (300 MHz, CDl$_3$OD) δ 1.15–1.70 (10H, m), 1.70–1.82 (2H, t), 1.97 (2H, t), 2.78–3.12 (5H, m), 3.35 (3H, m), 3.87 (2H, t), 4.03 (1H, m), 6.50 (1H, d), 6.69 (2H, m), 7.18 (3H, m), 7.41 (5H, bs).

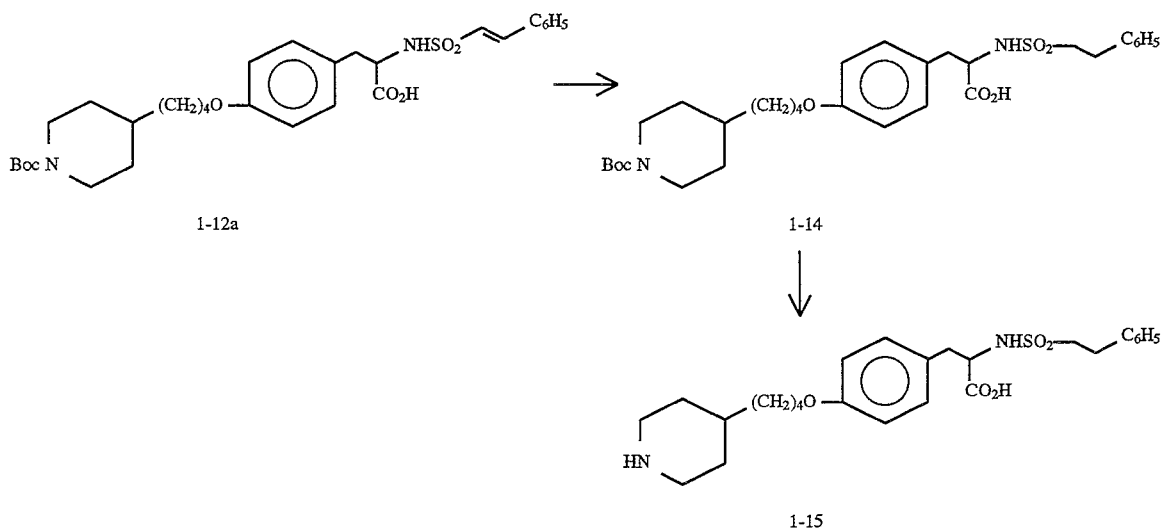

2-S-(2-Phenethylsulfonylamino)-3-[4-(N-t-butyloxycarbonylpiperidin-4-yl)butyloxyphenyl]propionic acid (1-14)

1-12a (0.21 g) was dissolved in 20 ml absolute ethanol, 0.1 g 10% Pd/C was added and the stirred suspension was hydrogenated under balloon pressure. After 4 hours the reaction was stopped and the solvent was removed to give the desired product 1-14 (0.194 g).

$^1$H NMR (300 MHz, CD$_3$OD) δ 1.05 (2H, m), 1.30–1.40 (3H, m), 1.47 (14H, m), 1.72 (5H, m), 2.67–2.93 (8H, m), 3.13 (1H, m), 3.31 (2H, m), 3.82 (2H, m), 4.00–4.20 (4H, m), 6.82 (2H, d), 7.07 (2H, d), 7.21 (5H, m).

2-S-(2-Phenethylsulfonylamino)-S-[4-(piperidin-4-yl)butyloxyphenyl]propionic acid hydrochloride (1-15)

1-14 (0.194 g) was dissolved in EtOAc and treated with HCl gas as described for 1-9 to provide pure 1-15 (0.145 g).

$^1$H NMR (300 MHz, CD$_3$OD) δ 1.25–1.68 (8H, m), 1.73 (2H, m), 1.93 (2H, m), 2.78 (3H, m), 2.91 (4H, m), 3.13 (1H, m), 3.33 (4H, m), 3.86 (2H, m), 4.18 (1H, m), 6.80 (2H, d), 7.09 (2H, d), 7.22 (5H, m).

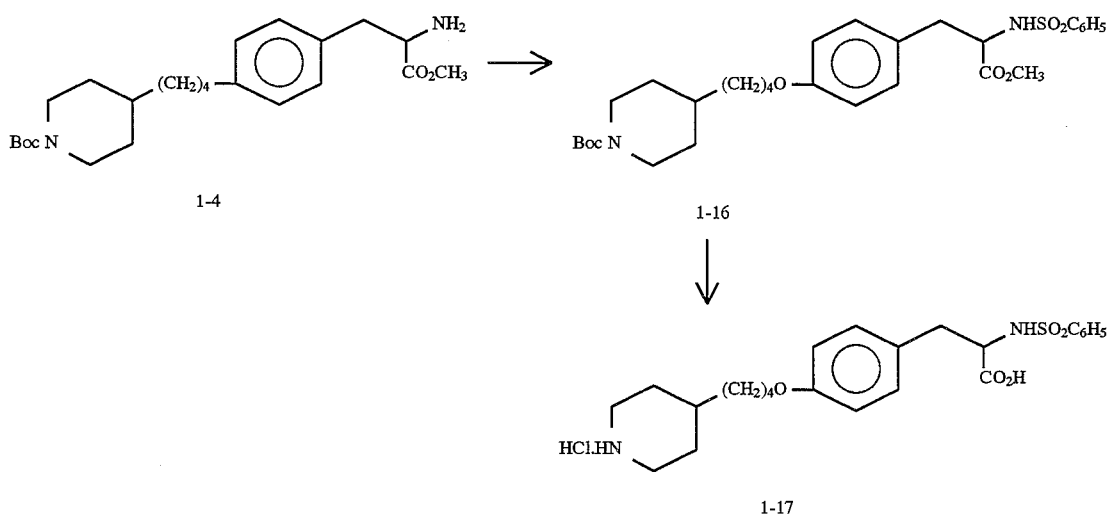

Methyl 2-S-(Phenylsulfonylamino)-3-[4-(N-t-butyloxycarbonylpiperidin-4-yl)butyloxyphenyl]propionate (1-16).

1-4 (0.647 g, 1.5 mmoles) was treated with phenylsulfonyl chloride (0.318 g, 1.8 mmoles) as described for 1-8. The crude product was purified by flash chromatography on silica gel eluting with CHCl$_3$(98)-MeOH(2) to give pure 1-16 (0.67 g).

$^1$H NMR (300 MHz, CDCl$_3$) δ 1.09 (2H, m), 1.25–1.40 (3H, m), 1.42 (9H, bs), 1.60–1.85 (6H, m), 2.66 (2H, m), 2.96 (2H, d), 3.55 (3H, s), 3.89 (2H, t), 4.09 (4H, m), 5.12 (1H, d), 6.72 (2H, d), 6.95 (2H, d), 7.40–7.65 (3H, m), 7.75 (2H, m).

2-S-(Phenylsulfonylamino)-3-[4-(piperidin-4-yl)butyloxyphenyl)propionic acid hydrochloride (1-17)

1-16 (0.525 g) was treated with lithium hydroxide as described for 1-8 to give crude product that was purified by flash chromatography on silica gel eluting with CHCl$_3$(97)-MeOH(3)-HOAc(1) to provide pure acid ($R_f$=0.2).

This acid was treated with HCl gas in EtOAc as described for 1-9 to provide pure 1-17.

$^1$H NMR (300 MHz, CD$_3$OD) δ 1.28–1.47 (6H, m), 1.50–1.70 (3H, m), 1.75 (2H, m), 1.97 (2H, d), 2.77 (1H, m), 2.95 (3H, m), 3.35 (4H, m), 3.93 (3H, m), 6.72 (2H, d), 7.02 (2H, d), 7.41 (2H, m), 7.52 (1H, m), 7.67 (2H, m).

(3H, 8), 3.91 (2H, t), 4.08 (2H, m), 4.29 (1H, m), 5.16 (1H, d), 6.78 (2H, d), 7.00 (4H, m), 7.55 (2H, dd).

2-S-(2-Thienylsulfonylamino)-3-[4-(piperidin-4-yl)butyloxyphenyl]propionic acid hydrochloride (1-19)

Treatment of 1-18 (0.22 g, 0.38 mmoles) with LiOH (0.045 g, 1.89 mmoles) as described for 1-8 provided the desired acid, which was purified by flash chromatography on silica gel eluting with CHCl$_3$(97)-CH$_3$OH(3)-HOAc(1).

$^1$H NMR (300 MHz, CD$_3$OD) δ 1.05 (2H, d t), 1.20–1.40 (5H, m), 1.40–1.60 (12H, m) 1.65–1.80 (5H, m), 2.65–2.82 (4H, m), 2.98 (1H, dd), 3.30 (1H, m), 3.92 (2H, t), 4.00–4.13 (5H, m), 6.75 (2H, d), 7.02 (3H, m), 7.39 (1H, d), 7.67 (1H, d).

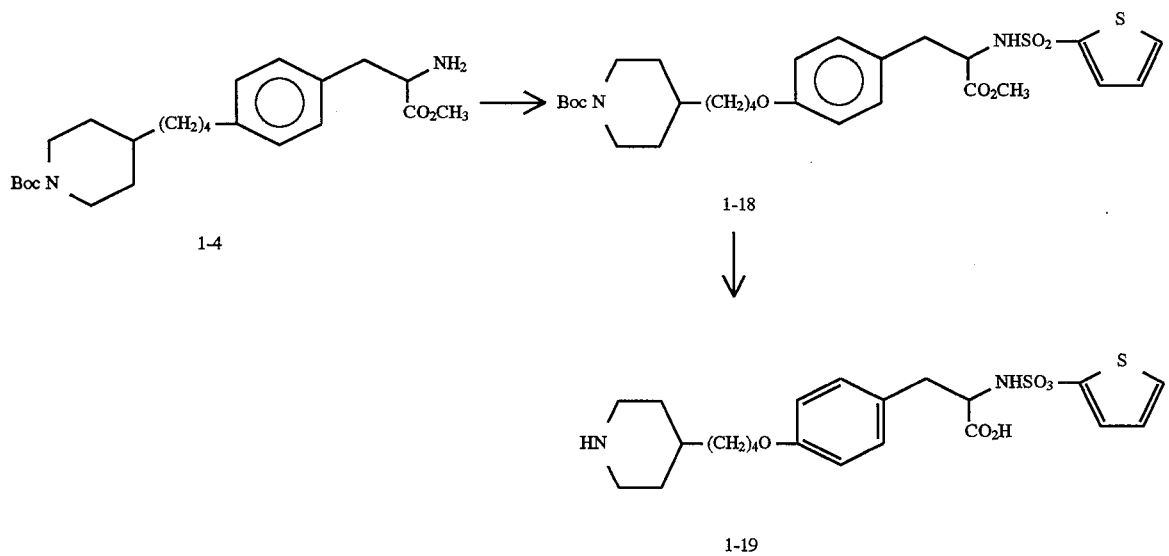

Methyl 2-S-(2-Thienylsulfonylamino)-3-[4-(N-t-butyloxycarbonylpiperidin-4-yl)butyloxyphenyl]propionate (1-18)

1-4 (0.304 g, 0.7 mmoles) was treated with 2-thienylsulfonyl chloride (0.155 g, 0.85 mmoles) as described for 1-8 to provide crude product. This was purified by flash chromatography on silica gel eluting with CHCl$_3$(98)-CH$_3$OH(2) to afford pure 1-18 as a viscous oil, $R_f$ 0.3 [silica gel, CHCl$_3$(98)-CH$_3$OH(2)]

$^1$H NMR (300 MHz, CDCl$_3$) δ 1.10 (2H, m), 1.31 (4H, m), 1.36–1.80 (16 H, m), 2.68 (2H, bt), 3.03 (2H, d), 3.57

Treatment of this acid with HCl gas as described for 1-9 provided 1-19 as a white solid after trituration.

Analysis Calcd. for C$_{22}$H$_{30}$N$_2$O$_5$S$_2$•HCl•0.5 H$_2$O: C, 51.60, H, 6.30, N, 5.47. Found: C, 51.57, H, 6.20, N, 5.51.
$^1$H NMR (300 MHz, CD$_3$OD) δ 1.29–1.45 (4H, m), 1.47–1.70 (3H, m), 1.71–1.83 (2H, m), 1.91–2.00 (2H, bd), 2.79 (1H, m), 2.90–3.04 (3H, m), 3.95 (2H, t), 4.04 (1H, m), 6.76 (2H, d), 7.05 (3H, m), 7.40 (1H, m), 7.79 (1H, m).

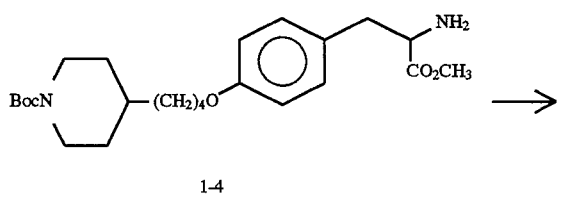

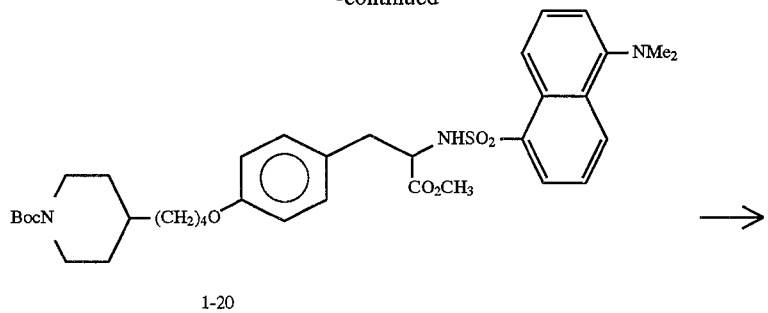

1-20

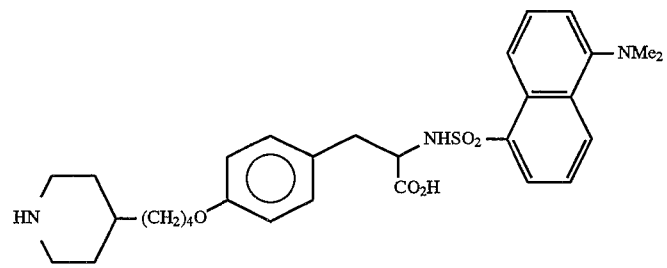

1-21

Methyl-2-S-(Dansylamino)-3-[4-(N-t-butyloxycarbonylpiperidin-4-yl)butyloxyphenyl]propionate (1-20)

1-4 (0.304 g, 0.7 mmoles) was treated with dansyl chloride (0.208 g, 0.77 mmoles) as described for 1-8 to provide crude product which was purified by flash chromatography on silica gel eluting with hexane(75)-EtOAc(25) to give pure 1-20. $R_f$ 0.25 (silica gel eluting with hexane(75)-EtOAc (25)).

$^1$H NMR (300 MHz, CDCl$_3$) δ 1.10 (2H, m), 1.21–1.38 (6H, m), 1.40–1.53 (11H, m), 1.60–1.80 (6H, m), 2.68 (2H, bt), 2.89 (6H, s), 3.33 (2H, s), 3.89 (2H, t), 4.05–4.19 (4H, m), 5.24 (1H, m), 6.62 (2H, d), 6.82 (2H, d), 7.18 (1H, d), 7.50 (2H, m), 8.19 (2H, t), 8.51 (1H, d).

2-S-(Dansylamino)-S-[4-(piperidin-4-yl)butyloxyphenyl]propionic acid hydrochloride (1-21)

Treatment of 1-20 (0.275 g, 0.412 mmoles) with LiOH as described for 1-8 gave the desired acid as a highly fluorescent viscous residue.

$^1$H NMR (300 MHz, CD$_3$OD) δ 1.09 (2H, m), 1.22–1.40 (3H, m), 1.40–1.57 (12H, m), 1.65–1.80 (3H, m), 2.60–2.80 (3H, m), 2.90 (6H, s), 3.31 (3H, m), 3.80 (2H, t), 3.90 (1H, m), 4.01–4.15 (4H, m), 6.47 (2H, d), 7.21 (1H, d), 7.42 (2H, m), 7.98 (1H, d), 8.20 (1H, d), 8.46 (1H, d).

Treatment of this acid in EtOAC with HCl gas as described for 1-9 provided 1-21 as a white solid upon ethylacetate trituration.

Analysis for C$_{30}$H$_{39}$N$_3$O$_5$S•1.8 HCl•H$_2$O: C, 56.53; H, 6.77; N, 6.59; Cl, 10.01. Found: C, 56.48; H, 6.66; N, 6.36; Cl, 10.21.

$^1$H NMR (300 MHz, CD$_3$OD) δ 1.30–1.51 (7H, m), 1.52–1.80 (4H, m), 1.95 (2H, bt), 2.65 (1H, m), 2.95 (3H, m), 3.30–3.40 (4H, m), 3.45 (6H, s), 3.84–3.97 (3H, m), 6.45 (2H, d), 6.77 (2H, d), 7.71 (2H, m), 8.00 (1H, d), 8.16 (2H, d), 8.55 (1H, d), 8.70 (1H, d).

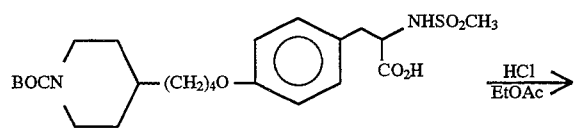

1-22

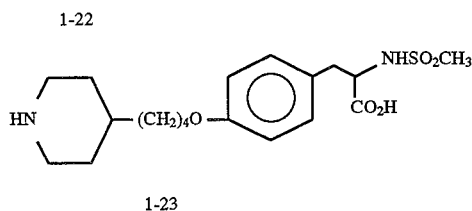

1-23

2-S-Methylsulfonylamino-3-[4-(piperidin-4-yl)butyloxyphenyl]propionic acid hydrochloride (1-23)

1-22 (0.39g, 0.78 mmoles), prepared from by sulfonylation with methane sulfonyl chloride is described for 1-20, was dissolved in EtOAc (20 ml) cooled to −78° and treated with HCl gas for 3 minutes. The reaction mixture was warmed to 0° over 30 minutes and the solvent was removed. The resulting residue was purified by flash chromatography to give pure 1-23 as a white solid. $R_f$ 0.54 (silica gel, 9:1:1 EtOH/H$_2$O/NH$_4$OH.

SCHEME 2

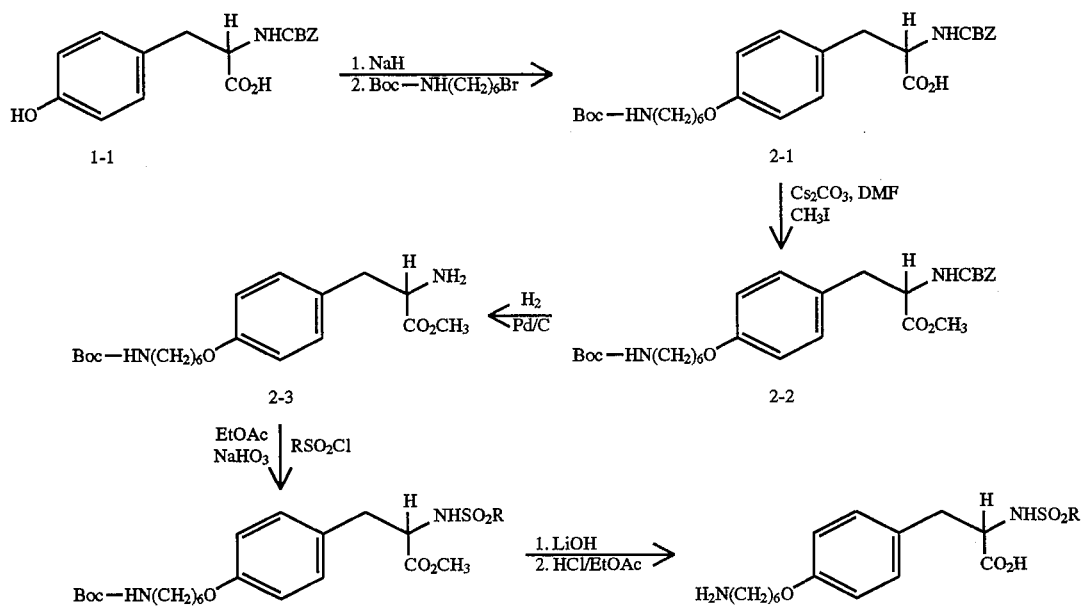

EXAMPLE 8

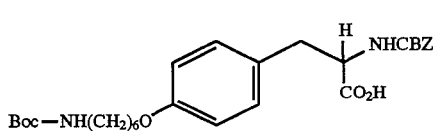

2-S-(Benzyloxycarbonylamino)-3-[4-(6-N-t-butyloxycarbonylaminohexyloxy)phenyl]propionic acid (2-1)

N-CBZ-L-tyrosine (15.0 g, 0.045 mole) was dissolved in 75 mL DMF and added at 0°–10° C. to a suspension of sodium hydride (2.16 g, 0.09 mole) in 25 mL DMF. The resulting suspension was stirred at 0°–10° C. for 1.0 hour and then 6-(t-butyloxycarbonylamino)hexyl bromide (12.6 g, 0.045 mole) in 25 mL DMF was added dropwise at 0°–5° C. and the clear, dark reaction mixture was stirred at room temperature overnight.

After solvent removal, the residue was taken up in EtOAc and this was made acidic with 10% KHSO$_4$ solution. The organic phase was separated, washed with brine, dried (Na$_2$SO$_4$) and the solvent removed to give an oil. This was purified by column chromatography on silica gel eluting with 98:2:1 CHCl$_3$/CH$_3$OH/HOAc to give pure 2-1 as a clear oil.

$^1$H NMR (300 MHz, CD$_3$OD) δ 1.45 (15H, m), 1.75(2H, m), 2.80–3.15 (6H, m), 3.91(2H, t), 4.38(1H, m), 4.95(6H, m), 6.85(2H,d), 7.06(2H,d)

EXAMPLE 9

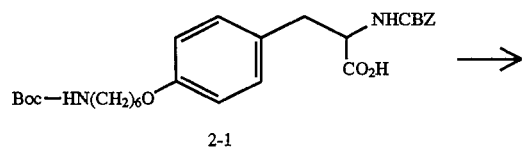

-continued

Methyl 2-S-(Benzyloxycarbonylamino)-3-[4-(6-N-t-butyloxycarbonylaminohexyloxy)phenyl]pripionate (2-2)

Compound 2-1 (10.0 g, 19.43 mmole) in 75 mL DMF was treated with cesium carbonate (3.16 g, 9.72 mmole) with stirring at room temperature for 1.9 hours. Then, methyl iodide (2.76 g, 19.43 mmole) was added dropwise and the reaction mixture was stirred overnight at ambient temperature. The solvent was removed at high vacuum (30° C.) and the residue was taken up in 300 mL EtOAc and washed with 2×40 mL protions of saturated NaHCO$_3$ solution, brine and dried (Na$_2$SO$_4$). Solvent removal provided 2-2 (8.5 g, 83%) as a clear oil.

$^1$H NMR (300 MHz, CDCl$_3$) δ 1.25–1.53 (16H, m), 1.76 (2H, m), 2.96–3.17 (4H, m), 3.71 (3H, s), 3.90 (2H, t), 4.61 (1H, m), 5.10 (2H, m), 5.19 (1H, m), 6.88 (2H, d), 6.98 (2H, d), 7.32 (5H, m).

EXAMPLE 10

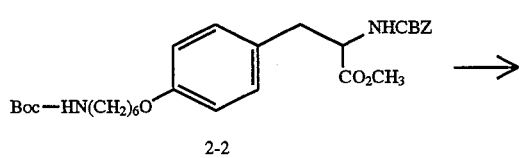

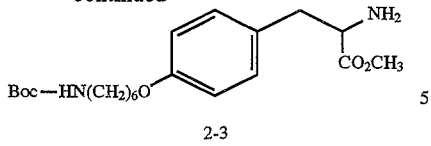

2-3

Methyl 2-S-Amino-3-[4-(6-N-t-butyloxycarbonylaminohexyloxy)phenyl]propionate (2-3)

Compound 2-2 (8.0 g, 15.1 mmole) was dissolved in 150 mL, absolute ethanol and 1.0 g 10% Pd/C was added. This suspension was hydrogenated in a Parr apparatus (50 psi) for 3.5 hours. The catalyst was then filtered off and the solvent removed on the rotary evaporator to give pure 2-3 (5.56 g) as a clear oil. $R_f$=0.4 on $SiO_2$ with 95:5 $CHCl_3/CH_3OH$ $^1$H NMR (300 MHz, CDCl$_3$) δ 1.30–1.55 (16H, m), 1.70 (2H, m), 2.80 (1H, m), 3.00–3.17 (3H, m), 3.71 (3H, s), 3.93 (2H, t), 6.82 (2H, d), 7.09 (2H, d).

EXAMPLE 11

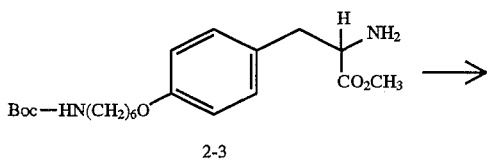

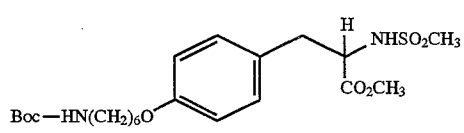

2-S-(Methylsulfonylamino)-3-[4-(6-N-t-butyloxycarbonylaminohexyloxy)phenyl]propionate (2-4)

2-3 (0.40 g, 1.01 mmole) was treated with methanesulfonyl chloride (0.116 g, 1.01 mmole) and NaHCO$_3$ (0.25 g, 3.0 mmole) as described for 1-8. The crude reaction product was purified by flash chromatography on silica gel eluting with 30% EtOAc/hexanes to give pure 2-4 (0.10 g) as a clear oil.

$^1$H NMR (300 MHz, CDCl$_3$) δ 1.36–1.56 (15H, m), 1.77 (2H, m), 2.70 (3H, s), 3.78 (3H, s), 3.92 (2H, t), 4.36 (1H, m), 4.90 (1H, d), 6.82 (2H, d), 7.09 (2H, d).

EXAMPLE 12

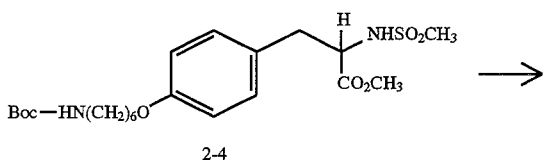

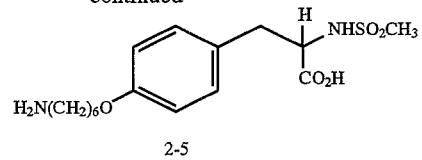

2-5

2-S-(Methylsulfonylamino)-3-[4-(6-aminohexyloxy)phenyl]propionic acid hydrochloride (2-5)

2-4 (0.1 g, 0.212 mmole) was treated with LiOH (0.026 g, 1.06 mmole) as described for 1-8 to provide 2-S-(methylsulfonylamino)-3-[4-(6-N-t-butyloxycazbonylaminohexyloxy)phenyl]propionic acid (0.125g) as a viscous oil.

$^1$H NMR (300 MHz, CD$_3$OD) δ 1.30–1.55 (16H, m), 1.75 (2H, m), 2.63 (3H, s), 2.85 (1H, dd), 3.0–3.13 (3H, m), 3.93 (2H, t), 4.17 (1H, m), 6.83 (2H, d), 7.20 (2H, d).

This acid was dissolved in EtOAc (20 mL) and treated with HCl gas as described for 1-9. Solvent removal provided a residue that was triturated with 30 mL Et$_2$O to provide pure 2-5 as a white solid (0.09 g).

$^1$H NMR (300 MHz, CD$_3$OD), δ 1.40–1.60 (4H, m), 1.60 (2H, m), 1.69 (2H, m), 2.68 (3H, s), 2.82 (1H, dd), 2.92 (2H, t), 3.10 (1H, dd), 3.30 (2H, m), 3.97 (2H, t), 4.18 (1H, m), 6.83 (2H, d), 7.19 (2H, d).

Analysis for $C_{16}H_{26}N_2O_5S\cdot HCl\cdot 0.25\ H_2O$ Calculated: C=48.11, H=6.94, N=7.01 Found: C=48.16, H=6.82, N=6.98.

EXAMPLE 13

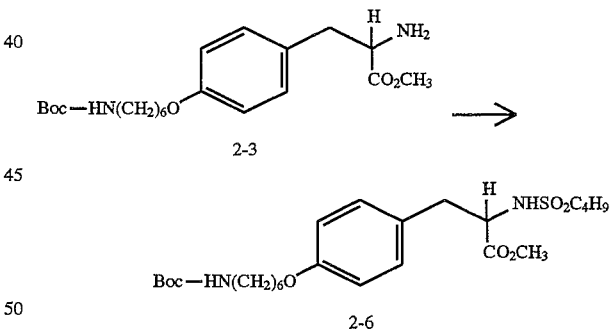

Methyl 2-S-(Butylsulfonylamino)-3-[4-(6-N-t-butyloxycarbonylaminohexyloxy)phenyl]propionate (2-6)

2-3 (0.40 g, 1.01 mmole) was treated with butylsulfonyl chloride (0.47 g, 3.03 mmole) and NaHCO$_3$ (0.50 g, 6.0 mmole) as described for 1-8. Crude reaction product was purified by flash chromatography on silica gel eluting with 30% EtOAc/hexanes to give pure 2-6 (0.22 g) as a clear oil.

$^1$H NMR (300 MHz, CDCl$_3$) δ 0.87 (3H, t), 1.35–1.54 (18 H, m), 1.61 (2H, m), 1.77 (2H, m), 2.74 (2H, t), 2.95 (1H, dd), 3.05–3.18 (3H, M), 3.90 (2H, t), 4.32 (1H, m), 4.72 (1H, m), 6.82 (2H, d), 7.07 (2H, d).

EXAMPLE 14

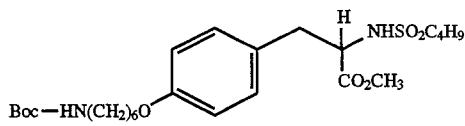

2-6

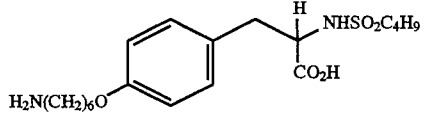

2-7

2-S-(Butylsulfonylamino)-3-[4-(6-aminohexyloxy) phenyl]propionic acid hydrochloride (2-7)

2-6 ( 0.2 g, 0.39 mmole) was treated in THF (1)/H$_2$O (1)/CH$_3$OH(1) solution with LiOH (0.05 g, 2.12 mmoles) as described for 1-8 to provide 2-S-(butylsulfonylamino)-3-[4-(6-N-t-butyloxycarbonylaminohexyloxy)phenyl]propionic acid (0.235 g) as a viscous oil.

$^1$H NMR (300 MHz, CD$_3$OD) δ 0.83 (3H, t), 1.35–1.56 (16H, m) 1.76 (2H, m), 2.61 (2H, t), 2.79 (1H, ddd), 3.00–3.14 (3H, m), 3.92 (2H, t), 4.11 (1H, m), 6.82 (2H, d), 7.18 (2H, d).

This acid (0.235 g, 0.7 mole) was dissolved in EtOAc (30 mL) and treated with HCl gas as described for 1-9. The residue was triturated with a solution of ether (40 mL)/EtOAC (10 mL) to provide 2-7 (0.17 g) as a white solid.

$^1$H NMR (300 MHz, CD$_3$OD) δ 0.85 (3H, t), 1.24 (2H, m), 1.35–1.60 (6H, m), 1.70 (2H, m), 1.80 (2H, m), 2.66 (2H, t), 2.78 (1H, dd), 2.92 (2H, t), 3.10 (1H, dd), 3.30 (1H, m), 6.85 (2H, d), 7.20 (2H, d).

Analysis for C$_{19}$H$_{32}$N$_2$O$_5$S.HCl Calculated: C=52.22, H=7.61, N=6.41 Found: C=51.80, H=7.61, N=6.33.

EXAMPLE 14A

2-S-(Butylsulfonylamino)-3-[4-(6-acetamidinohexyloxy)phenyl]propionic acid (2-7a)

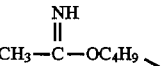

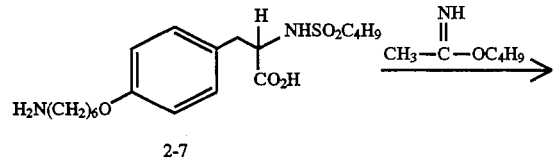

2-7a

A solution of 2-7 (1.0 g, 2.29 mmole) in THF (30 ml) is treated with ethyl acetimidate (0.2 g, 2.29 mmol) and the resulting reaction mixture is stirred at room temperature for 16 hours. The solvent is then removed and the residue is recrystallized from ethyl acetate to give pure 2-7a.

EXAMPLE 14B

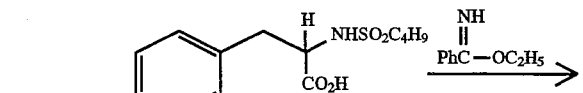

2-7

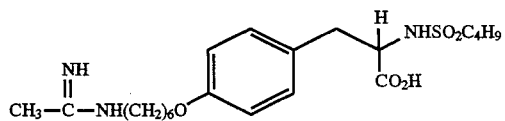

2-7b

2-S-(Butylsulfonylamino)-3-[4-(6-benzamidinohexyloxy)phenyl]propionic acid (2-7b)

A solution of 2-7 (1.0 g, 2.29 mmole) in THF (30 ml) is treated with ethyl benzimidate (0.34 g, 2.29 mmole) and the resulting solution is stirred at room temperature for 20 hrs. The solvent is removed and the residue is taken up in EtOAc, filtered and recystallized to give pure 2-7b.

EXAMPLE 14C

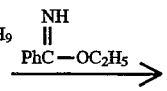

2-7

2-7c

2-S-(Butylsulfonylamino)-3-[4-(6-guanidinohexyloxyphenyl]propionic acid (2-7c)

A mixture of 2-7 (1.0 g, 2.29 mmol) and N-nitrosomethylthioguanidine (0.32 g, 2.29 mmol) is heated at 40° for 5 minutes in absolute EtOH (15 ml) and then is allowed to stand for 1 day at room temperature. The solvent is removed in vacuo and the residue is purified by flash chromatography on silica eluting with CHCl$_3$(95)-CH$_3$OH (5)-HOAc(2) to give the desired nitroguanidino intermediate.

This is dissolved in 10% HCl-CH$_3$OH (20 ml) and shaken in a Parr apparatus (50 psi) in the presence of 10% Pd-C (100 mg) at room temperature for 8 hours. The catalyst is then removed by filtration, the solvent is removed in vacuo, and the residue dissolved in 10% aqueous HCl solution and heated at reflux for 2 hours. The solvent is removed in vacuo and the residue purified by chromatography on a Dowex 1-X2 column eluting with water to give pure 2-7c.

EXAMPLE 15

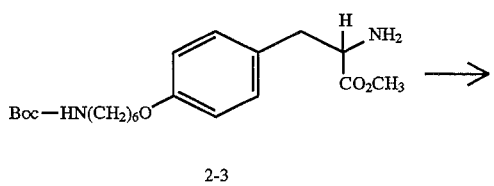

Methyl 2-S-(Benzylsulfonylamino)-3-[4-(6-N-t-butyloxycarbonylaminohexyloxy)phenyl]propionate (2-8)

2-3 (0.29 g, 0.735 mmole) was treated with benzylsulfonyl chloride (0.14 g, 0.735 mmole) and NaHCO$_3$ (0.185 g, 2.2 mmole) as described for 1-8. The crude reaction product was purified by flash chromatography on silica gel eluting with 1:1 hexanes/EtOAc to give pure 2-8 (0.27 g) as a clear oil.

$^1$H NMR (300 MHz, CDCl$_3$) δ 1.47–1.69 (15H, m), 1.90 (2H, m), 2.18 (2H, s), 3.08 (2H, d), 3.25 (2H, m), 3.85 (3H, s), 4.05 (2H, t), 4.19–4.20 (4H, m), 4.80 (1H, d), 6.83 (2H, d), 7.12 (2H, d), 7.47 (5H, m).

EXAMPLE 16

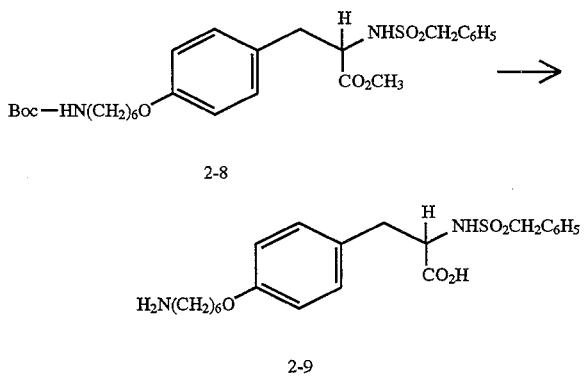

2-S-(Benzylsulfonylamino)-S-[4-(6-aminohexyloxy)phenyl]propionic acid hydrochloride (2-9)

2-8 (0.48 g, 0.875 mmole) was treated with LiOH (0.105 g, 4.37 mmole) as described for 1-8 to give 2-S-(benzylsulfonylamino)-3-[4-(6-N-t-butyloxycarbonylaminohexyloxy)phenyl]propionic acid (0.4 g) as a foam.

$^1$H NMR (300 MHz, CD$_3$OD) δ 1.30–1.52 (15H, m), 1.72 (2H, m), 2.81 (1H, dd), 3.00 (3H, m), 3.93 (2H, m), 4.06 (2H, m), 6.81 (2H, d), 7.13 (2H, d), 7.20–7.32 (5H, m).

This acid (0.4 g, 0.75 mmole) was dissolved in EtOAc (30 mL) and treated with HCl gas as described for 1-9. Crude reaction product was triturated with ether to give pure 2-9.(0.35 g) as a white solid.

$^1$H NMR (300 MHz, CD$_3$OD) δ 1.38–1.57 (4H, m), 1.65 (2H, m), 1.73 (2H, m), 2.71 (1H, dd), 2.89 (2H, t), 3.02 (1H, dd), 3.30 (3H, m), 3.94–4.15 (5H, m), 6.83 (2H, d), 7.15 (2H, d), 7.29 (5H, m).

EXAMPLE 16 A

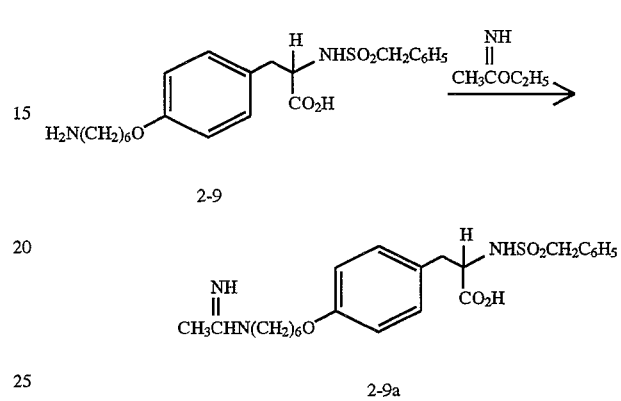

2-S-(Benzylsulfonylamino)-3-[4-(6-(acetamidinohexyloxy-phenyl)]propionic acid (2-9a)

A solution of 2-9 (1.0 g, 2.1 mmol) in THF (30 ml) is treated with ethyl acetimidate (0.18 g, 2.1 mmol) an described in Example 14A to give pure 2-9a after recrystallization from ethyl acetate.

EXAMPLE 16B

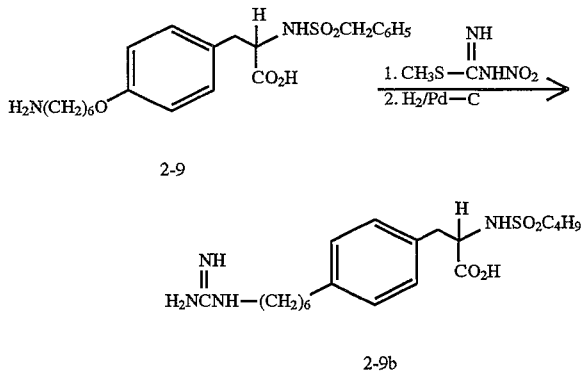

2-S-(Benzylsulfonylamino)-S-[4-(6-(guanidinohexyloxy)phenyl]propionic acid (2-9b)

A mixture of 2-9 (1.0 g, 2.1 mmol) and N-nitrosomethylthioguanidine (0.29 g, 2.1 mmol) is treated as described for Example 14C to give pure 2-9b.

SCHEME 3

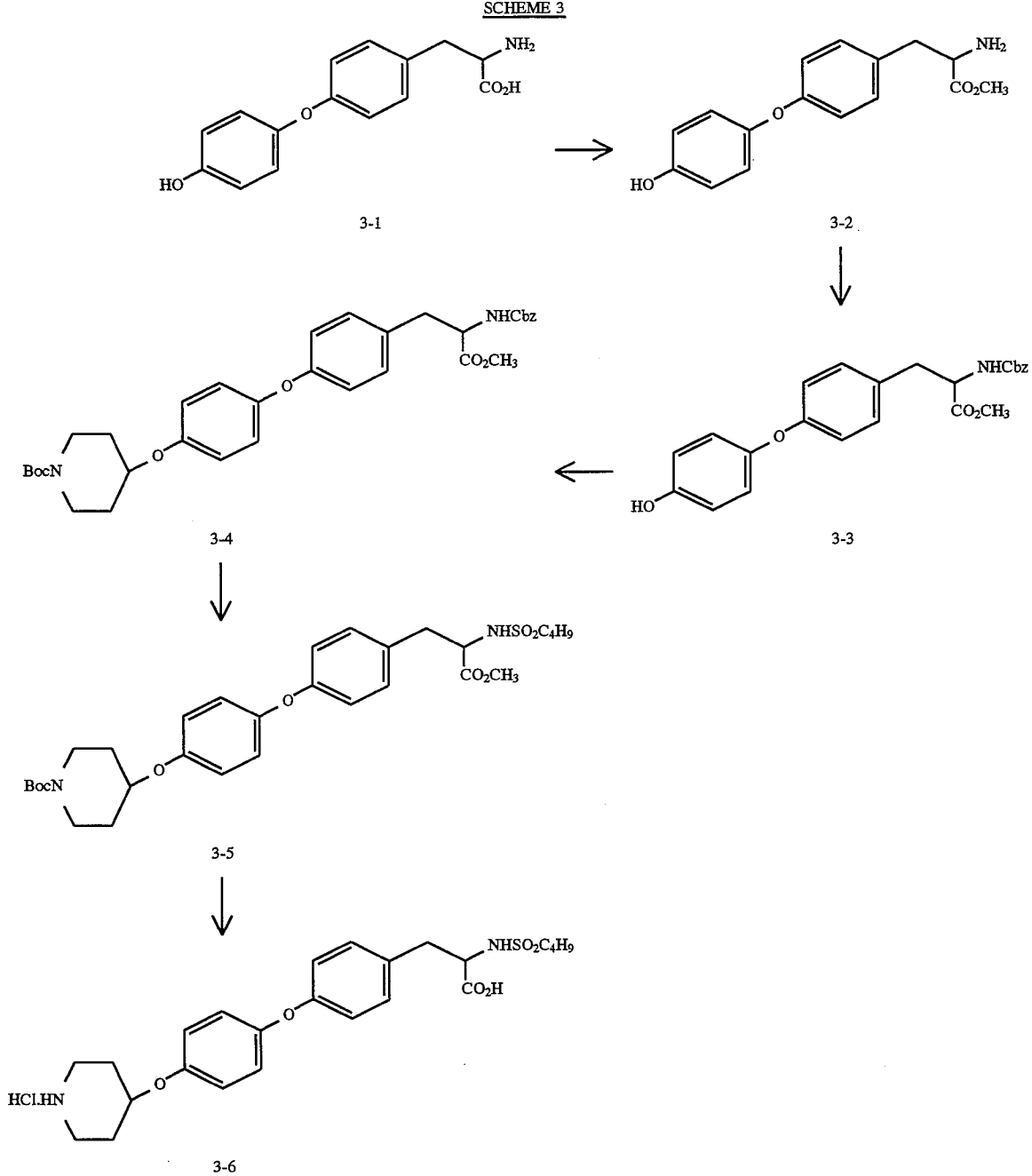

Methyl 2-S-amino-3-[4-(4-hydroxyphenyl)oxyphenyl]propionate (3-2)

CH$_3$OH (100 ml) was cooled to 0° and treated with SOCl$_2$ (47 mmol) with stirring for 15 minutes at 0° and then 3-1 (1.5 g, 5.49 mmol) was added with stirring for 16 hours as the temperature rose to ambient.

The reaction mixture was filtered and the solvent was removed to give an oil that provided 3-2 (1.57 g) after ether washing.

$^1$H NMR (300 MHz, CD$_3$OD) δ 3.10–3.30 (2H, m), 3.81 (3H, s), 6.76–6.90 (6H, m), 7.20 (2H, d).

Methyl 2-S-(N-Benzyloxycarbonylamino)-3-[4-(4-hydroxyphenyl)oxyphenyl]propionate (3-3)

A water(1)-dioxane(1) solution (10 ml) of 3-2 (0.2 g, 0.62 mmol) was cooled to 0° C. and treated with Na$_2$CO$_3$ (0.131 g, 1.23 mmole) and benzylchloroformate (0.619 mmol). After 1.5 hours of vigorous stirring, the dioxane was removed at low pressure and the residue diluted with H$_2$O and extracted with EtOAc. The organic extract was washed with brine, dried (Na$_2$SO$_4$) and the solvent removed to provide 3-3 as an oil.

$^1$H NMR (300 MHz, CDCl$_3$) δ 3.06 (2H, m), 3.75 (3H, s), 4.64 (1H, m), 5.10 (2H, m), 5.36 (1H, m), 6.83 (6H, m), 7.00 (2H, d), 7.37 (5H, bs).

Methyl-2-S-(N-Benzyloxycarbonylamino)-3-[4-(4-N-t-butyloxycarbonylpiperidin-4-yl)oryphenyloxy]phenyl-propionate (3-4)

A benzene (40 ml) solution of 3-3 (0.5 g, 1.18 mmol) was treated with N-t-butyloxycarbonylpiperidin-4-ol (0.24 g, 1.18 mmol) and Ph$_3$P (0.310 g, 1.18 mmol) while stirring at room temperature with constant N$_2$ purging. Diethyl azodicarboxylate (1.18 mmol) was added and the resulting solution was stirred at room temperature for 16 hours.

The solvent was then removed and the residue was purified by flash chromatography on silica gel eluting with hexane(70)-EtOAc(30) to provide pure 3-4.

$^1$H NMR (300 MHz, CDCl$_3$) δ 1.48 (9H, s), 1.80 (2H, m), 1.95 (2H, m), 3.08 (2H, m), 3.36 (2H, m), 3.76 (3H, s), 4.40 (1H, m), 4.63 (1H, m), 5.10 (1H, m), 5.25 (1H, m), 6.80–7.04 (8H, m), 7.36 (5H, bs).

Methyl 2-S-(Butylsulfonylamino)-3-[4-(4-N-t-butyl-oxycarbonylpiperidin-4-yl)oxyphenyloxy]phenylpropionate (3-5)

A solution of 3-4 (0.5 g, 0.082 mmol) EtOH (40 ml) was treated with 10% Pd/C (125 mg) and this suspension hydrogenated in a Parr flask at 50 psi for 1.5 hour. The catalyst was filtered off and the solvent removed to give the desired amino ester as a clear oil.

$^1$H NMR (300 MHz, CDCl$_3$) δ 1.48 (9H, s), 1.50–1.80 (8H, m), 1.91 (2H, m), 2.82 (1H, m), 3.04 (1H, m), 3.34 (2H, m), 3.76 (3H, s), 4.20 (1H, m), 7.90 (8H, m), 8.11 (2H, d).

This amino ester (0.36 g, 0.77 mmol) was dissolved in EtOAc (10 ml) and treated with NaHCO$_3$ (0.386 g, 4.6 mmol) and n-butylsulfonylchloride (1.53 mmol) with heating at reflux for 48 hours. The solvent was removed and the residue purified by flash chromatography on silica gel eluting with hexane(65)-EtOAc(35) to provide pure 3-5 as an oil.

$^1$H NMR (300 MHz, CDCl$_3$) δ 0.88–1.02 (4H, m), 1.25–1.45 (3H, m), 1.50 (9H, s), 1.51–1.80 (2H, m), 1.93 (2H, m), 2.80 (2H, m), 2.95–3.20 (2H, m), 3.21–3.40 (2H, m), 3.72 (2H, m), 3.74 (3H, s), 4.38 (2H, m), 4.80 (1H, d), 6.90 (6H, m), 7.10–7.27 (2H, m).

2-S-(Butylsulfonylamino)-3-[4-(piperidin-4-yl)oxyphenyloxy]phenylpropionic acid hydrochloride (3-6)

A solution of 3-5 (0.2 g, 0.34 mmol) in THF(1)-H$_2$O(1)-CH$_3$OH(1) was treated with LiOH (0.075 g, 1.78 mmol) at room temperature for 8 hours. The solvent was removed and the residue was acidfied with 10% KHSO$_4$ solution and this extracted several times with EtOAc. The organic extracts were combined, washed with brine, dried (NaSO$_4$) and the solvent removed to give the desired acid. R$_f$=0.3 [silica gel, 97(CHCl$_3$)-3(CH$_3$OH)-1(HOAc)].

$^1$H NMR (300 MHz, CDCl$_3$) δ 0.85 (3H, t), 1.20–1.30 (3H, m), 1.46 (9H, s), 1.50–2.0 (6H, m), 2.75 (2H, m), 2.97 (1H, m), 3.18 (1H, m), 3.33 (2H, m), 3.76 (2H, m), 4.35 (2H, m), 5.07 (1H, m), 6.89 (6H, m), 7.13 (2H, m).

This acid (0.15 g, 0.26 mmol) was dissolved in EtOAc and treated with HCl gas as described for 1-9to give pure 3-6 as a white solid.

$^1$H NMR (300 MHz, CD$_3$OD) δ 0.89 (3H, t), 1.32 (2H, m), 1.53 (2H, m), 1.97–2.21 (4H, m), 2.75 (2H, m), 2.63 (1H, m), 3.20 (3H, m), 3.40 (2H, m), 4.14 (1H, m), 6.82–7.05 (6H, m), 7.23 (2H, m).

SCHEME 4

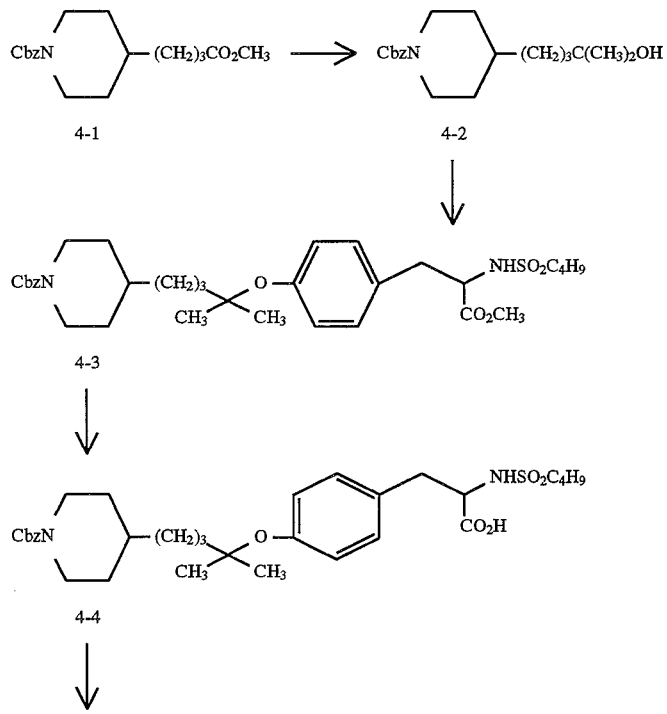

-continued
SCHEME 4

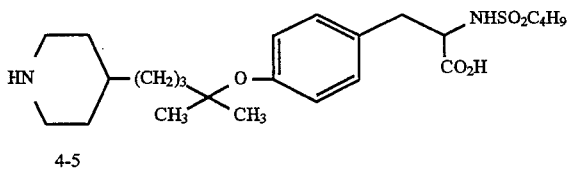

4-5

4[4-(N-Benzyloxycarbonylpiperidin-4-yl)-2-methyl]-pentan-2-ol (4-2)

Methyl 4-(N-Benzyloxycarbonylpiperidin-4-yl)-butanoate (4-1) (10.07 g, 0.032 mol) in THF (200 ml) was cooled to 0° C. and treated with CH₃MgI (0.095 mol) for 3.0 hours. The reaction mixture was poured into ice, acidified with 10% KHSO₄ and extracted with 3 portions of EtOAc. The combined organic extract was washed with brine, dried (MgSO₄) and the solvent removed. The residue was purified by flash chromatography on silica gel eluting with hexane (7)-EtOAc(3) to give pure 4-2. R$_f$=0.3 (silica gel, hexane (7)-EtOAc(3)).

Methyl 2-S-(Butylsulfonylamino)-3-[4-(N-Benzyloxycarbonylpiperidin-4-yl)-2,2-dimethyl]butyloxyphenyl-propionate (4-3)

N-n-Butylsulfonyl-L-tyrosine methyl ester (7.21 g, 0.023 mole) was dissolved in a mixture of 4-2(1.0 g), CH₂Cl₂ (30 ml) and benzene (250 ml). Triphenylphosphine (5.97 g, 0.023 mole) was added and after purging with N₂, diethyl azodicarboxylate (3.6 ml, 0.023 mole) was added at room temperature as the reaction mixture turned red-orange in color. Reaction mixture stirred at room temperature for 7 days. Solvent was removed and the residue was purified by flash chromatography on silica gel eluting with hexane(60)-EtOAc(40) to give pure 4-3.

¹H NMR (300 MHz, CDCl₃) δ 0.88 (6H, t), 1.10–1.40 (12H, m), 1.43–1.78 (8H, m), 2.70–2.82 (4H, m), 2.95–3.10 (3H, m), 3.75 (3H, s), 4.18 (2H, m), 4.32 (1H, m), 5.13 (2H, s), 6.88 (2H, d), 7.06 (2H, d), 7.38 (5H, m).

2-S-(Butylsulfonylamino)-S-[4-(N-Benzyloxycarbonylpiperidin-4-yl)-2,2-dimethyl]butyloxyphenylpropionic acid (4-4)

Dissolved 4-3 (0.64 g, 0.001 mole) in THF/H₂O/CH₃OH mixture and treated with LiOH (0.26 g, 0.0062 mole) at room temperature for 8 hours. Solvent removal, acidification (KHSO₄ solution) and EtOAc extraction provided crude 4-4 which was purified by flash chromatography on silica gel eluting with CHCl₃ (97)-CH₃OH(3)-HOAc(1) to give pure 4-4.

¹H NMR (300 MHz, CDCl₃) δ 0.86 (6H, s), 1.05–1.50 (13H, m), 1.55–1.80 (5H, m), 2.77 (4H, m), 3.04 (2H, m), 4.10 (2H, bd), 4.17 (1H, m), 4.85 (1H, d), 5.14 (2H, s), 6.88 (2H, d), 7.13 (2H, d), 7.39 (5H, m).

2-S-(Butylsulfonylamino)-3-[4-(piperidin-4-yl)-2,2-dimethyl]butyloxyphenylpropionic acid (4-5)

To ammonium formate (0.23 g, 3.65 mmol) in CH₃OH (5 ml) was added 4-4 (0.22 g, 3.65 mmole) in 10 ml CH₃OH and then 10% Pd/C (100 mg) was added at room temperature. After 15 minutes the reaction mixture was passed thru a Solka Floc pad and the solvent removed. This residue was purified by flash chromatography on silica gel eluting with EtOH(9)-H₂O(1)-NH₄OH(1) to give pure 4-5.

¹H NMR (300 MHz, CD₃OD) δ 0.88 (6H, s), 1.15–1.40 (12H, m), 1.42–1.70 (7H, m) 1.90 (2H, d), 2.78–3.00 (6H, m), 3.06 (1H, dd), 3.35 (3H, m), 3.93 (1H, m), 6.86 (2H, d), 7.20 (2H, d).

SCHEME 5

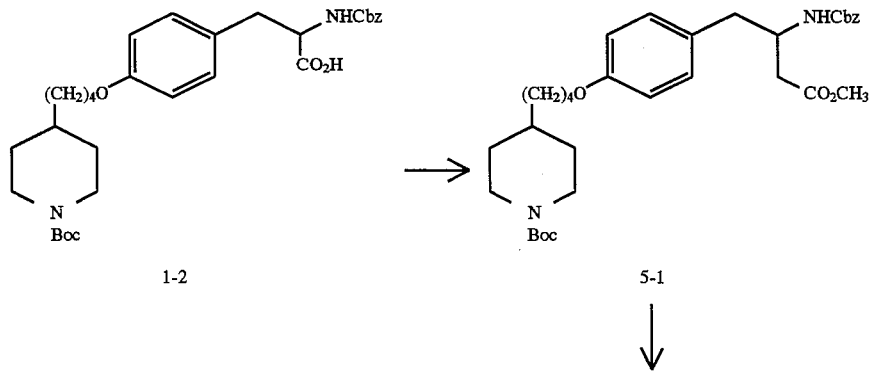

-continued
SCHEME 5

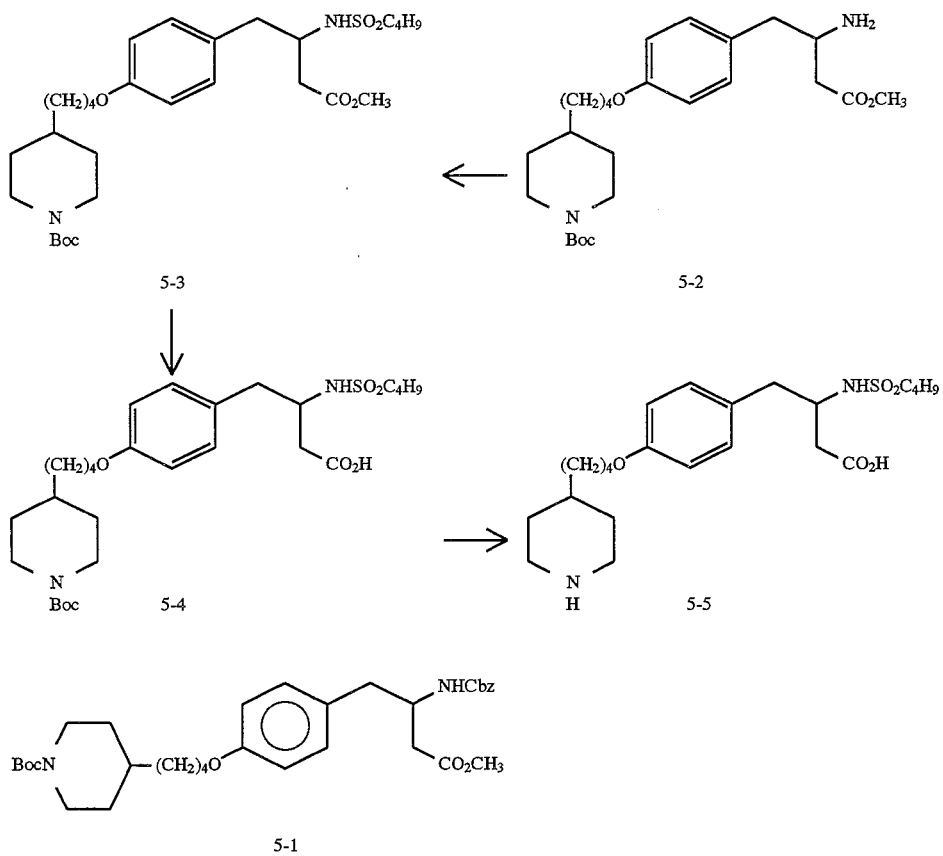

Methyl 3-S-(Benzyloxycarbonylamino)-4-[4-(N-t-butyl-oxycarbonylpiperidin-4-yl)butyloxyphenyl] butyrate (5-1)

A solution of compound 1-2 (1.0 g, 1.8 mmole) and N-methylmorpholine (0.21 mL, 1.9 mmole) in EtOAc (10 mL) was stirred at −15° C. and treated with isobutyl chloroformate (0.24 mL, 1.8 mmole). After 15 minutes the heterogeneous mixture was treated portion-wise with an ethereal solution of diazomethane (0.5M:10 mL, 5.0 mmole), followed by continued stirring at 0° for 1.0 hour. The reaction mixture was then purged with argon for 10 minutes to remove excess diazomethane. The organic phase was washed with 2×5 mL portions of $H_2O$, brine, dried ($MgSO_4$), and evaporated. The residue was then dissolved in $CH_3OH$ (15 mL) and treated sequentially with triethylamine (0.7 mL, 5.0 mmole) and $AgO_2CPh$ (110 mg, 0.5 mmole) while stirring at ambient temperature to effect vigorous gas evolution. After 30 minutes the solvent was evaporated and then the crude reaction product purified by flash chromatography on silica gel eluting with 4:1 hexane/EtOAc to give 5-1 (0.52 g) as an oil. TLC $R_f$=0.23 (30% EtOAc/hexane)

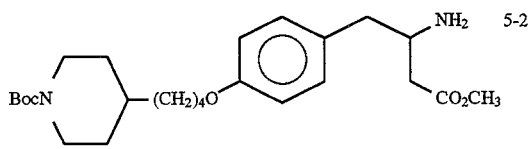

Methyl 3-S-Amino-4-[4-(N-t-butyloxycarbonylpiperidin-4-yl)butyloxyphenyl] butyrate (5-2)

To 5-1 (0.52 g, 0.9 mmole) dissolved in absolute ethanol (20 mL) was added 10% Pd/C (0.25 g) and the resulting suspension was hydrogenated under balloon pressure for 12 hours. The catalyst was then filtered off and the solvent was removed in vacuo to give 5-2 (0.35 g) as an oil.

TLC $R_f$=0.15 (9:1:1 $CH_2Cl_2/CH_3OH/AcOH$).

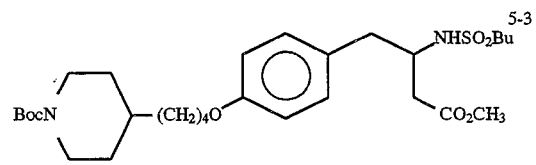

Methyl 3-S-(Butylsulfonylamino)-4-[4-N-t-butyloxycarbonylpiperidin-4-yl)butyloxyphenyl] butyrate (5-3)

To 5-2 (0.36 g, 0.8 mmole), triethylamine (170 μL, 1.2 mmole), 4-dimethylaminopyridine (12 mg, 0.1 mmole), and THF (5 mL) at 0° C. was added n-butyl-sulfonyl chloride (130 μL, 1.0 mmole) with stirring. The cooling bath was removed and stirring was continued for 6 hours. The reaction mixture was diluted with 10 mL of EtOAc and then washed with 2×5 mL $H_2O$, brine, dried ($MgSO_4$), and concentrated. The crude reaction product was purified by flash chromatography on silica gel eluting with 4:1 hexane/EtOAc to give 5-3 (180 mg) as an oil.

¹H NMR (300 MHz, CDCl₃) δ 1.12 (2H, m), 1.25–1.83 (13H, m), 1.29 (3H, t), 1.47 (9H, s), 2.68 (6H, m), 2.87 (2H, d), 3.73 (3H, s), 3.93 (2H, t), 4.08 (1H, m), 4.72 (1H, d), 6.87 (2H, d), 7.12 (2H, d).

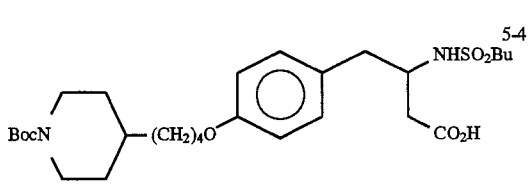

3-S-(Butylsulfonylamino)-4-[4-N-t-butyloxycarbonyl-piperidin-4-yl)butyloxyphenyl]butanoic acid (5-4)

Compound 5-3 (175 mg, 0.33 mmole) in CH₃OH (4.0 mL) was treated with 1N NaOH (1.0 mL, 1.0 mmole) followed by continued stirring at ambient temperature for 20 hours. The reaction mixture was diluted with 15 mL EtOAc and then washed with 10 mL 5% KHSO₄ and brine, dried (MgSO₄), and concentrated to give 5-4 (160 mg) as an oil.

TLC R_f=0.31 (9:0,5:0.5 CH₂Cl₂/CH₃OH/AcOH).

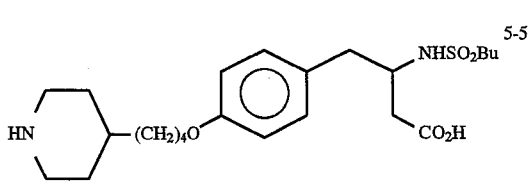

3-S-(Butylsulfonylamino)-4-[4-piperidin-4-yl)butyloxyphenyl]butanoic acid (5-5)

To a stirred solution, of compound 5-4 (160 mg, 0.30 mmole), CH₂Cl₂ (2.0 mL), and anisole (100 μL) at 0° C. was added CF₃CO₂H (1.0 mL). After 1.5 hours at 0° C. the solvents were evaporated and the crude reaction product purified by flash chromatography on silica gel eluting with 10:0.8:0.8 ethanol/H₂O/conc. NH₄OH to give 5-5 (42 mg) as a solid.

¹H NMR (300 MHz, D₂O/CF₃CO₂D) δ 0.82 (3H, t), 1.10–1.70 (11H, m), 1.80 (m, 2H), 1.98 (m, 2H), 2.48 (2H, t), 2.72 (3H, m), 3.00 (3H, m), 3.43 (2H, m), 3.96 (1H, m), 4.10 (2H, t), 7.01 (2H, d), 7.32 (2H, d).

SCHEME 6

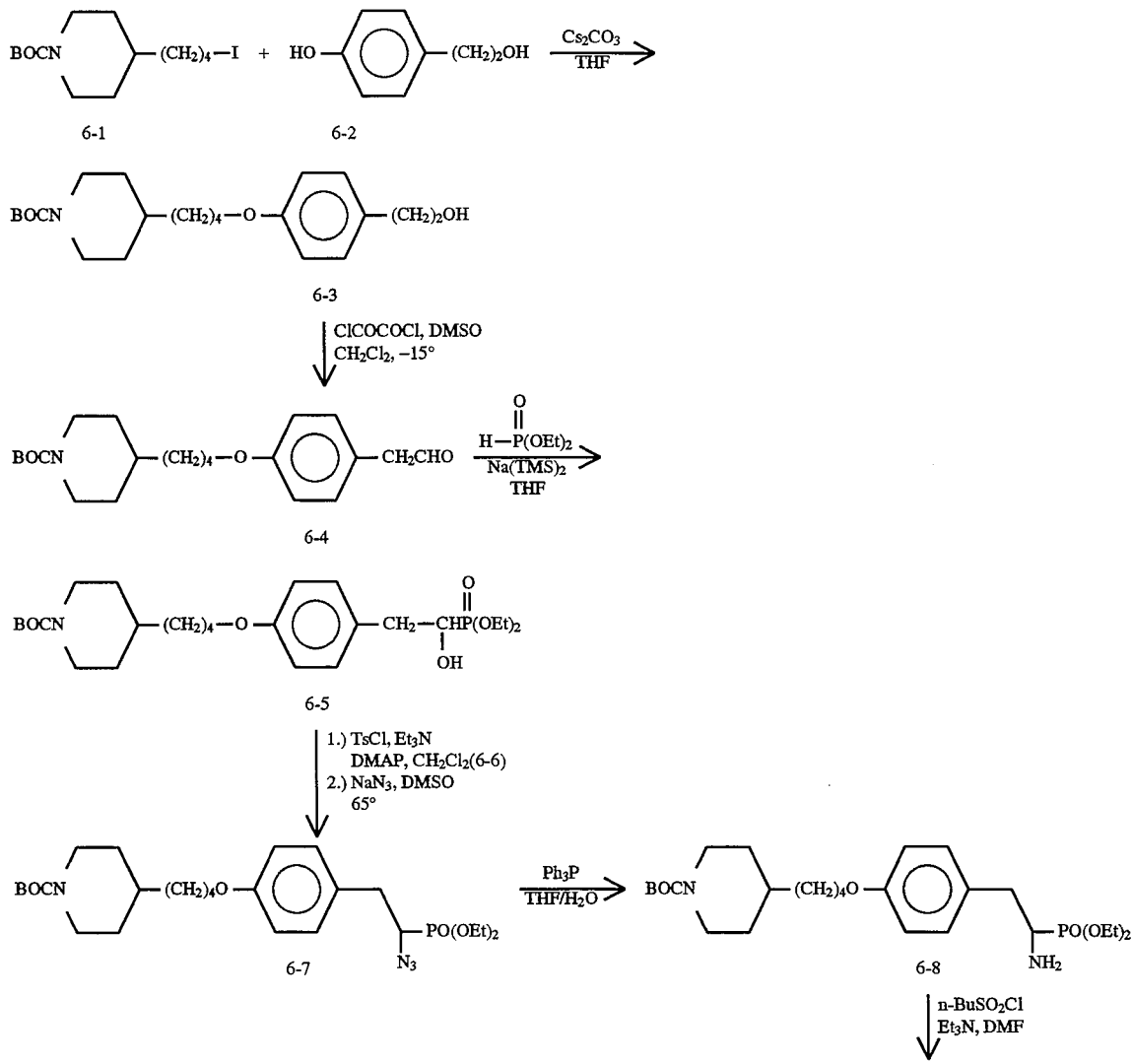

-continued
SCHEME 6

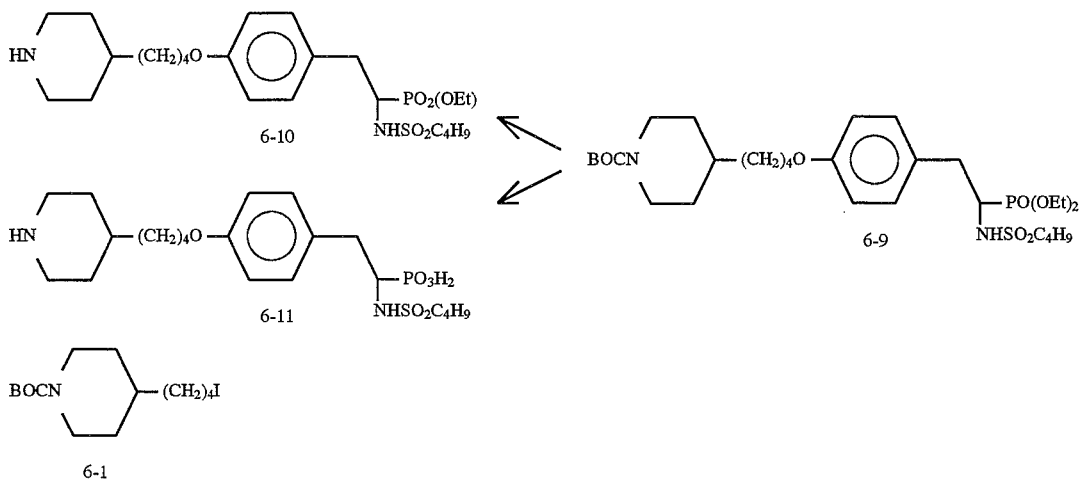

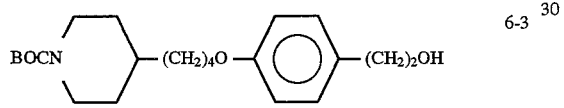

4-(N-t-Butyloxycarbonylpiperidin-4-yl)butyliodide (6-1)

This was prepared from 2-piperidineethanol as described for the corresponding bromide except that $Ph_3P/I_2$ was used in the final step to generate the desired iodide.

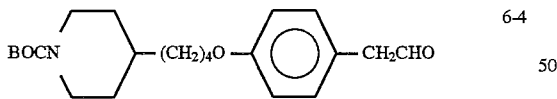

4-[4-(N-t-Butyloxycarbonylpiperidin-4-yl)butyloxyphenyl]ethanol (6-3)

A mixture of 6-1 (4.55 g, 12.4 mmol), 4-hydroxyphenylethanol (6-2) (1.88 g, 13.6 mmol) and $Cs_2CO_3$ (4.04 g, 12.4 mmol) in DMF (20 ml) was stirred at 23° for 16 hours. The mixture was diluted with $Et_2O$, washed with $H_2O$ (3×50 ml) and the ether layer was dried ($MgSO_4$) and concentrated. This residue was purified by flash chromatography on silica gel eluting with 5% acetone/$CH_2Cl_2$ to give 6-3. $R_f$ 0.24 (silica gel, 5% acetone/$CH_2Cl_2$).

4-[4-(N-t-Butyloxycarbonylpiperidin-4-yl)butyloxyphenyl]acetaldehyde (6-4)

A solution of oxalyl chloride (2.66 g, 20.97 mmol) in $CH_2Cl_2$ (25 ml) cooled to −15° was treated with a solution of DMSO (3.57 g, 45.74 mmol) in CH2Cl2 (5 ml) and this was stirred for 2 minutes. Then, 6-3 (3.6 g, 9.54 mmol) in $CH_2Cl_2$ (10 ml) was added with stirring at −15° for 5 minutes and then at room temperature. Mixture was diluted with $Et_2O$ (300 ml) and washed with $H_2O$ (200 ml) and the organic phase was dried and concentrated. The residue was purified by flash chromatography on silica gel eluting with 10% acetone/$CH_2Cl_2$ to give pure 6-4. Rf 0.50 (silica gel, 5% acetone/$CH_2Cl_2$).

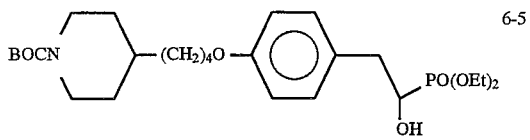

{2-[4-[4-(N-t-Butyloxycarbonylpiperidin-4-yl) butyloxyphenyl]-1-hydroxy]}ethanephosphonic acid diethyl ester (6-5)

A solution of 6-4 (32.8 mg, 0.087 mmol), and diethylphosphite (18.0 mg, 0.131 mmol) in TEF (5 ml) was cooled to 0° and treated with $NaN(TMS)_2$ (0.131 mmol) with stirring for 8 hours. The reaction mixture was diluted with $Et_2O$, washed with 1M $NaHSO_4$ solution, brine, dried ($MgSO_4$) and the solvent removed. The mixture was purified by flash chromatography on silica gel eluting with 25% acetone/$CH_2Cl_2$ to give pure 6-5. $R_f$ 0.31 (silica gel, 25% acetone/$CH_2Cl_2$).

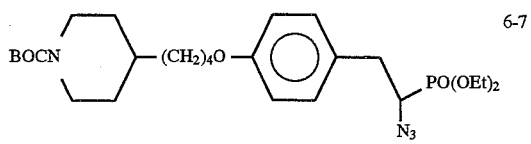

{2-[4-[4-(N-t-Butyloxycarbonylpiperidin-4-yl) butyloxyphenyl]-1-azido}ethanephosphonic acid diethyl ester (6-7)

A solution of 6-5 (51.3 mg, 0.1 mmol) in $CH_2Cl_2$ (5 ml) was treated with $Et_3N$ (0.125 mmol) and DMAP (0.01 mmol) and at 0° TsCl (23.8 mg, 0.125 mmol) was added and the resulting solution was stirred at room temperature for 18 hours. The solvent was removed and the residue purified by flash chromatography on silica gel eluting with 7% acetone/ $CH_2Cl_2$ to provide pure rosylate (6-6).

A solution of 6-6 (66.1 mg, 0.10 mmol) in DMSO (2 ml) was treated with $NaN_3$ (13 mg, 0.20 mmol) and this was heated at 65° for 20 hours. The cooled reaction mixture was then poured into a mixture of ether (50 ml) and brine (5 ml) and the organic phase was washed with brine, dried ($MgSO_4$) and the solvent removed. This residue was purified by flash chromatography on silica gel eluting with 10% isopropanol/hexane to give pure 6-7. $R_f$ 0.28 (silica gel, 10% IPA/hexane).

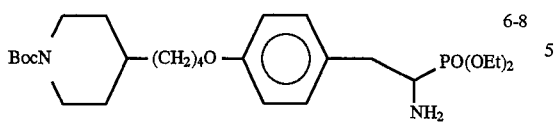

{2-[4-[4-(N-t-Butyloxycarbonylpiperidin-4-yl)butyloxyphenyl]-1-amino]}ethanephosphonic acid diethyl ester (6-8)

A solution of 6-7 (0.31 g, 0.575 mmol) in THF (10 ml)/$H_2O$ (0.5 ml) was treated at rt with $Ph_3P$ (0.6 g, 2.30 mmol) with stirring for 48 hrs. Solvent removal gave a residue that was purified by flash chromatography in silica gel eluting with 30% IPA/hexane to give pure 6-8. $R_f$ 0.22 (silica gel, 30% IPA/hexane).

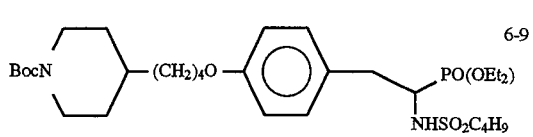

{2-[4-[4-(N-t-Butyloxycarbonylpiperidin-4-yl)butyloxyphenyl]-1-n-butylsulfonylamino]}ethanephosphonic acid diethyl ester (6-9)

A solution of 6-8 (0.17 g, 0.33 mmol) in DMF (1 ml) at 0°–5° was treated with $Et_3N$ (1.84 mmol) and n-$C_4H_9SO_2Cl$ (0.78 g, 0.495 mmol) in DMF (2 ml) with stirring for 2.0 hours. The reaction mixture was poured into $H_2O$ (10 ml)/$Et_2O$ (50 ml) and the organic phase was separated, washed with 1N $KHSO_4$, satd. $NaHCO_3$, brine, and dried $MgSO_4$. Solvent removal provided 6-9.

$^1$H NMR (300 MHz, $CDCl_3$) δ 0.83 (3H, t), 1.15 (3H, m), 1.35 (4H, m), 1.45 (9H, s), 1.62 (3H, m), 2.30 (2H, t), 2.68 (2H, bt), 2.79 (1H, m), 3.20 (1H, m), 3.91 (2H, t), 4.00 (1H, m), 4.10 (2H, m), 4.18 (2H, m), 4.94 (1H, m), 6.83 (2H, d), 7.19 (2H, d).

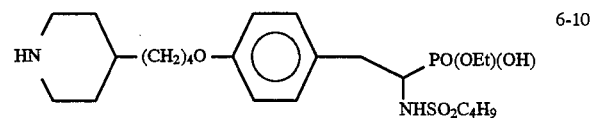

{2-[4-[4-(Piperidin-4-yl)butyloxyphenyl]-1-n-butylsulfonylamino]}ethanephosphonic acid ethyl ester (6-10)

A solution of 6-9 (0.09 g, 0.142 mmol) in $CH_2Cl_2$ cooled to 0° was treated with TMSBr (0.054, 0.355 mmol) and the resulting solution was stirred at rt for 16 hours with cooling. $Et_3N$ (100 μl) was added and the solvent was removed. The residue was dissolved in 10% aqueous acetone (5 ml), concentrated, and suspended in toluene to give a solid. This was purified by flash chromatography on silica gel eluting with 10:1:1 EtOH/$H_2O$/$NH_4OH$ to give pure 6-10.

$^1$H NMR (300 MHz, $CD_3OD$) δ 0.84 (3H, t), 1.18 (3H, m), 1.27 (3H, t), 1.42 (6H, m), 1.75 (2H, m), 1.93 (2H, bd), 2.25 (2H, m), 2.63 (1H, m), 2.93 (2H, m), 3.20 (1H, m), 3.35 (4H, m), 3.70 (2H, m), 3.98 (4H, m), 6.82 (2H, d), 7.21 (2H, d).

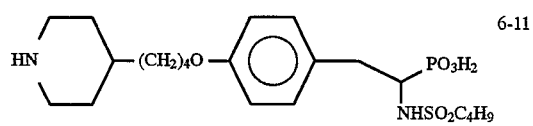

{2-[4-[4-(Piperidin-4-yl)butyloxyphenyl]-1-n-butylsulfonylamino]}ethanephosphonic acid (6-11)

A solution of 6-9 (0.63 g, 0.142 mmol) in $CHCl_3$ (5 ml) at rt was treated with TMSBr (0.85 mmol) for 16 hrs. The solvent was removed and the residue was dissolved in 10% aqueous acetone and this stripped to dryness. The residue was mixed with toluene and the resulting gum was purified by flash chromatography on silica gel eluting with 4:1:1 EtOH/$H_2O$/$NH_4OH$ to provide pure 6-11. $R_f$ 0.38 (silica gel, 4:1:1EtOH/$NH_4OH$/$H_2O$.

SCHEME 7

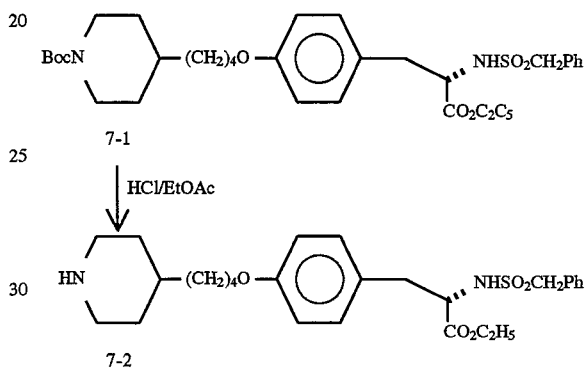

Ethyl 2-S-Benzylsulfonylamino-3-[4-(N-t-butyloxycarbonylpiperidin-4-yl)butyloxyphenyl]propionate (7-1)

This compound was prepared analogously to 1-10 employing the appropriate ethyl ester.

Ethyl 2-S-Benzylsulfonylamino-3-[4-(piperidin-4-yl)butyloxyphenyl]propionate (7-2)

A solution of 7-1 (0.79 g, 1.30 mmol) in EtOAc (75 ml) was cooled to −30° and treated with HCl gas for 25 minutes. Solvent removal provided pure 7-2 as a white solid.

Analysis Calcd: C, 58.39; H, 7.41; N, 5.04. Found: C, 58.36; H, 7.34; N, 4.89.

In the above Schemes and Examples, various reagent symbols have the following meanings:
BOC: t-butoxycarbonyl.
Pd-C: Palladium on activated carbon catalyst.
DMF: Dimethylformamide.
CBZ: Benzyloxycarbonyl.
BOP: Benzotriazol-1-yloxytris(dimethylamino) phosphonium hexafluorophosphate.
EtOAc: ethyl acetate
DMF: dimethylformamide
$CH_2Cl_2$: methylene chloride
$CHCl_3$: chloroform
MeOH: methanol
HOAc: acetic acid
DMAP: 4-Dimethylaminopyridine Suitable alternative protecting groups that can be used in the preparation of the present invention include benzyl ester, cyclohexyl ester, 4-nitrobenzyl ester, t-butyl ester, 4-pyridylmethyl ester, benzyloxycarbonyl, isonicotinyloxycarbonyl, O-chlorobenzyloxycarbonyl, p-nitrobenzyloxycarbonyl, p-methoxybenzyloxycarbonyl, t-amyloxycarbonyl, isobornyloxycarbonyl, adamantyloxycarbonyl, 2-(4-biphenyl)-2-propyloxycarbonyl and 9-fluorenylmethoxycarbonyl.

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

$$R^1-(CH_2)_m-X-Y-Z-\underset{\underset{R^5}{(CH_2)_p}}{\overset{\underset{R^2}{\overset{R^3}{|}}-\underset{|}{N}-SO_2-R^4}{(CH_2)_n}}$$

with phenyl ring bearing $R^6$ and $R^7$ substituents on the $(CH_2)_n$ chain.

| Example | R⁷ | X | Y | Z | m | n | p |
|---|---|---|---|---|---|---|---|
| 18 | —CH₃ | —C≡C— | $\underset{—CH—}{\overset{C_6H_5}{|}}$ | — | 1 | 1 | 1 |
| 19 | —C₆H₅ | $\underset{CH_2CN}{\overset{CH_3}{\underset{|}{—C=C—}}}$ | $\underset{—C—NH—}{\overset{O}{\|}}$ | —CH₂— | 2 | 3 | 1 |
| 20 | —H | $\underset{—CH—}{\overset{CHOCH_3}{\|}}$ | $\underset{—NHC—}{\overset{O}{\|}}$ | $\underset{—CH—}{\overset{OCH_3}{\|}}$ | 4 | 1 | 1 |
| 21 | —OCH₃ | $\underset{\underset{\|}{—N—C—}}{\overset{C_6H_5}{\underset{O}{\|}}}$ | —CH₂— | $\underset{—CH—}{\overset{OH}{\|}}$ | 6 | 2 | 2 |
| 22 | —H | $\underset{\underset{\|}{—C—NH—}}{\overset{O}{\underset{C_6H_3}{\|}}}$ | —CH₂— | —O— | 5 | 1 | 5 |
| 23 | —CH₃ | pyrrolidinone ring | $\underset{—CH—}{\overset{CH_3}{\|}}$ | —S— | 5 | 2 | 2 |

-continued
| Example | R¹ | R² | R³ | R⁴ | R⁵ | R⁶ |
|---|---|---|---|---|---|---|
| 24 |  | 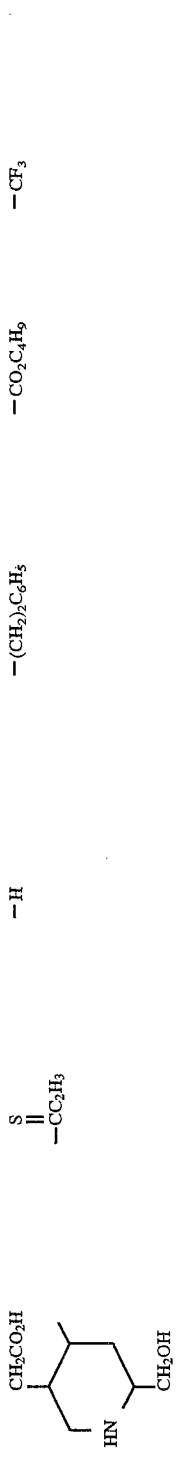 | —H | —(CH$_2$)$_2$C$_6$H$_5$ | —CO$_2$C$_4$H$_9$ | —CF$_3$ |
| 25 | 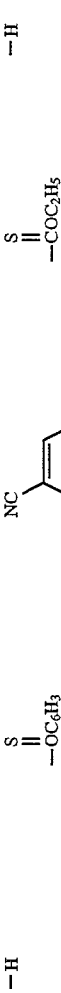 | —H | 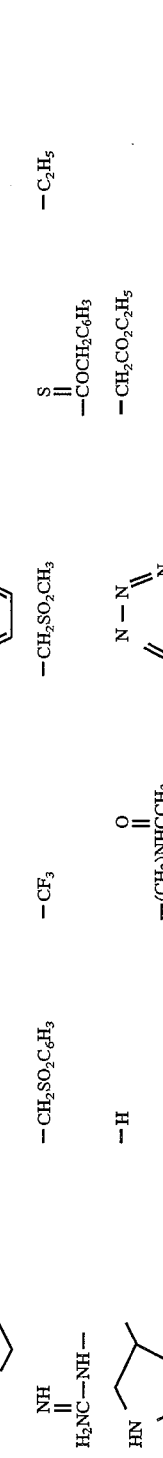 |  | 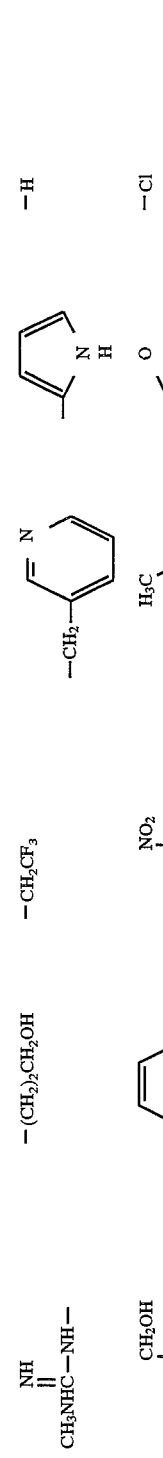 | —H |
| 26 | 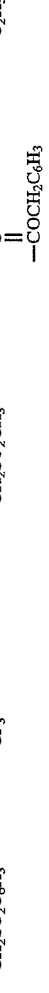 | —CH$_2$SO$_2$C$_6$H$_5$ | —CF$_3$ | —CH$_2$SO$_2$CH$_3$ |  | —C$_2$H$_5$ |
| 27 | 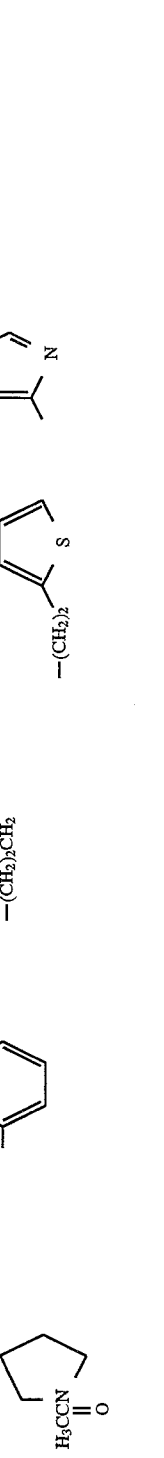 | —H | 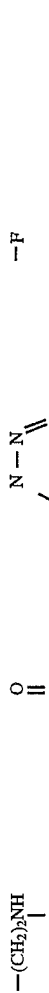 | 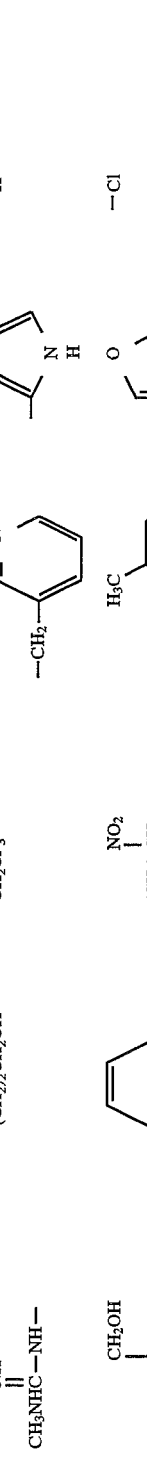 |  | |
| 28 | 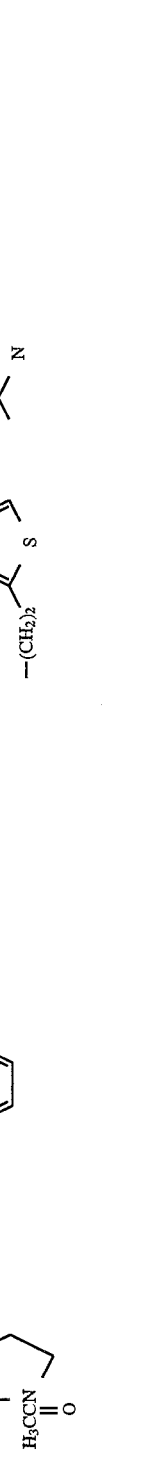 | —(CH$_2$)$_2$NHCH$_2$C$_6$H$_3$ |  |  | —F | —H |
| 29 |  | —(CH$_2$)$_2$CH$_2$OH | —CH$_2$CF$_3$ | —CH$_2$— |  | |
| 30 |  |  |  |  |  | —Cl |

-continued

| Example | 31 |
|---|---|
| | R7: ![piperidinyl]-CH2CH2OCH2 |
| | X: -CH2CH |
| | Y: -H |
| | Z: -CH2C(=O)-pyridinyl |
| | -CO2H |
| | -CH2C6H5 |

| Example | R7 | X | Y | Z | m | n | p |
|---|---|---|---|---|---|---|---|
| 24 | -H | -O- | C4H9-CH- | -SO- | 2 | 4 | 3 |
| 25 | -OCH3 | O=C- | CH2C6H3-CH- | -SO2- | 1 | 3 | 1 |
| 26 | -CN | S=C- | CO2C6H3-CH- | -NH- | 2 | 2 | 2 |
| 27 | -H | (1,3-diazinan-2-one) | -O- | 4 | 3 | 3 | 3 |
| 28 | -CH3 | CH2C6H3-N-CH2- | C6H3-N- | CH3-N- | 1 | 1 | |
| 29 | -H | -S- | CH3-CH- | CH2C6H3-N- | 0 | 5 | 5 |
| 30 | -(CH2)2C6H5 | (pyrrolidin-2-one) | C6H3-CH- | C4H9-N- | 3 | 2 | 1 |
| 31 | -H | CN-CH- | -O- | — | 1 | 2 | 4 |

-continued

| Example | R¹ | R² | R³ | R⁴ | R⁵ | R⁶ |
|---|---|---|---|---|---|---|
| 32 | (structure: CH₃, N, CH₃, HN ring) | —H | —(CH₂)CN | —C₈H₁₇ | (structure: N=N, N-CH₃ ring with ethyl) | —C₃H₇ |
| 33 | C₆H₅CH₂NHC(=NH)— | —CH₂OC₆H₅ | —C₃H₇ | | —CO₂CH₃ | —H |
| 34 | (structure: O-containing ring with CH₃, NH) | -t-Bu | —CH₂C₆C₅ | —(CH₂)₂C(=S)CH₃ | —CO₂H | —CH₃ |
| 35 | (structure: CH₂C₆H₃, N ring with H₃C, CH₃CN) | (pyridinyl) | —H | —CH₃ | —CO₂ | —C₂H₅ |
| 36 | (structure: H₃C, O, N-CH₃, HOH₂C ring) | —H | (2,4-dimethylpyridinyl) | —(CH₂)₃NH₂ | —CO₂C₄H₉ | —OC₃H₇ |
| 37 | H₂N—C(=N-CN)— | —H | —C₄H₉ | —(CH₂)₂NHCCH₃ (O) | —CO₂H | —CH₂C₆H₅ |
| 38 | (structure: imidazole with CH₃, CH₃, N-CH₃) | —CH₂C₆H₅ | —H | —(CH₂)₄OCH₃ | —CO₂C₂H₅ | —CH₃ |

-continued

| | R⁷ | X | Y | Z | | | —CH₂SO₂CH₃ |
|---|---|---|---|---|---|---|---|
| 39 | (N–N–NH ring with CH₃) | —(CH₂)₂OCH₃ | —C₂H₅ | —CH₂CH(NO₂)CH₂C₆H₅ | $\overset{O}{\underset{\|}{-P(OH)_2}}$ | | |

| Example | R⁷ | X | Y | Z | m | n | p |
|---|---|---|---|---|---|---|---|
| 32 | —H | —CH₂— | —CH(CH₂CO₂CH₃)— | —C(=O)— | 8 | 2 | 8 |
| 33 | —H | 4-pyridyl—CH— | imidazolidine-2-thione—N,N— | —C(=S)—C— | 3 | 1 | 3 |
| 34 | —Br | —C(=S)— | (3-pyridyl)—N— | —C≡C— | 1 | 1 | 1 |
| 35 | —H | —CH₂— | —N(CH₃)— | —C(=O)— | 2 | 1 | 2 |
| 36 | —H | —C(CH₃)(H)— | —N(CH₂CH₃)— | —C≡C— | 1 | 2 | 1 |
| 37 | —H | —C(CH₃)(C₂H₅)— | —O— | —C(CH₃)=C(CH₃)— | 0 | 0 | 5 |
| 38 | —OCH₃ | —O— | —NCH₃ | —C(C₂H₅)=CH— | 6 | 0 | 6 |
| 39 | —H | | —CH(CH₃)— | — | | | |

-continued

| Example | R¹ | R² | R³ | R⁴ | R⁵ | R⁶ |
|---|---|---|---|---|---|---|
| 40 | CH₃CH₂NH—C(=N—CH₃)—NH— | 4-methylpyridin-2-yl-CH₂— | —CH₃ | —CH₂CH₂CO₂-i-pr | —P(=O)(OH)₂ | pyridinyl |
| 41 | 4-methylpiperidin-1-yl-C(=NH)(CH₃)— | —CH₂SO₂CH₃ | —C₆H₅ | — | —P(=O)(OCH₃)₂ | —F |
| 42 | H₅C₂—NH— | 4-methylpyridinyl | —CH₂CO₂CH₃ | 5-(4-methylphenyl)thiophen-2-yl | —P(=O)(OC₂H₅)(OH) | —CN |
| 43 | H₂N—C(=NCH₂C₂H₅)—NH— | —CH₂SC₆H₅ | —CH₂OCH₅ | 4-methyl-1H-1,2,4-triazol-3-yl-CH₂ | —P(=O)(OCH₃C₆H₅)₂ | —C₂H₅ |
| 44 | Et₂N— | —CH₂OC₃H₇ | —H | —(CH₂)₃CH₂OH | —CO₂H | —H |
| 45 | 3-methylpyrrolidin-1-yl | —(CH₂)₂SCH₃ (C=O) | —OC₂H₅ | —(CH₂)₄CO₂H | —CO₂-i-pr | —CH₂CN |
| 46 | 1-methyl-4-aminopiperidinyl | —(CH₂)₂NNHCH₃ | —CF₃ | —(CH₂)₃C(=S)—C₂H₅ | —CO₂C₆H₅ | —CH₃ |
| 47 | (F₃CH₂C)HN— | —H | —C₃H₇ | 4-methyl-6-(CH₂CF₃)pyridin-2-yl | —CO₂H | —CO₂CH₃ |
| 48 | H₂N— | -t-Bu | —H | 4-chlorocyclohexa-1,3-dien-1-yl | —CO₂CH₃ | —F |

| Example | R⁷ | X | Y | Z | m | n | p |
|---|---|---|---|---|---|---|---|
| 40 | —CH₃ | —NH | —SO₂ | —O— | 2 | 4 | 1 |
| 41 | —OH | —NCH₂C₆H₅ | —SO₂ | —C(=O)— | 3 | 1 | 0 |

-continued

| | R¹ | R² | R³ | R⁴ | | | |
|---|---|---|---|---|---|---|---|
| 42 | -H | -C(=S)- | -H | -CH₂- | 1 | 1 | 1 |
| 43 | -H | -CH₂- | -C(=S)- | -C(=O)-NHC- | 3 | 4 | 1 |
| 44 | -CF₂CF₃ | -O- | -CH₂- | -C(=O)-NHC- | 2 | 0 | 10 |
| 45 | -H | H₃C F / -C=C- | -C(=O)-N(CH₃)- | -SO₂- | 1 | 3 | 1 |
| 46 | -OH | -C(=O)-N(CH₃)- | -CH₂- | — | 10 | 2 | 2 |
| 47 | -H | -CH₂- | -CH(OH)- | -C(=S)- | 0 | 2 | 4 |
| 48 | -CF₃ | -NH- | -CH₂- | -C(=O)- | 3 | 1 | 2 |

| Example | R¹ | R² | R³ | R⁴ | R⁵ | R⁶ |
|---|---|---|---|---|---|---|
| 49 | CH₃NH-C(=NHCH₃)- | -CH₂CC(=O)CH₃ | -H | (N=C(CH₃)-O- with CH₂OCH₃) | -CO₂C₂H₅ | -CH₂NO₂ |
| 50 | H₂NC(=NH)-NH- | -CH₂SC₆H₅ | -CH₃ | -C₂H₅ | -CO₂C₃H₇ | -H |
| 51 | C₂H₅O₂CCH₂CH₂-NH | -CF₃ | -H | -C₄H₇ | -CO₂CH₂C₆H₅ | p-CH₃-C₆H₄- |
| 52 | (imidazol-2-yl)-CH₂NH- | -CH₃ | -H₂CC(=S)-C₆H₅ | -C₅H₁₁ | -CO₂CC(=O)CH₃ | -OC₄H₉ |

-continued

| Ex | (col A) | (col B) | (col C) | (col D) | (col E) |
|---|---|---|---|---|---|
| 53 | $H_3C$-pyridyl-$(CH_2)_2HN-$ | $-CH_2CN$ | $-C_6H_{13}$ | $-CO_2COCH_3$ (C=S) | $-CCH_3$ (C=S) |
| 54 | $H_5CCHNH_2CH_2CN-$ (C=S), $CH_3$ | $-CH_2CF_3$ | $-H$ | $-CO_2COC(CH_3)_3$ (C=O) | $-H$ |
| 55 | $H_5C_6CHNH_2CH_2CN-$ (C=O), $H_5C_6H_2C$ | pyridyl (N=) with NH | $-C_8H_{17}$ | $-CNHCH_2CO_2H$ (C=O) | $-C_6H_5$ |
| 56 | $F_3C$-cyclopentyl-$CH_2-NH-$ | $-H$ | $-C_2H_5$ | $CNHCHCO_2CH_3$ (C=O), $C_6H_5$ | $-CCH_3$ (C=S) |
| 57 | HOOCH$_2$C–N–$H_3COOC(CH_2)_2$ | $-H$ | $-CH_2C_6H_5$ | $-CNHCHCO_2C_2H_5$ (C=O), $CH_3$ | $-CF_3$ |
|    |                            |     | $-(CH_2)_2C_6H_5$ | $-(CH_2)_2-O-C_6H_5$ |    |

| Example | $R^7$ | X | Y | Z | m | n | p |
|---|---|---|---|---|---|---|---|
| 49 | $-H$ | $-CH_2-$ | $-CH_2-$ | — | 2 | 2 | 2 |
| 50 | $-CH_2NHCCH_3$ (C=O) | $-CH_2-$ | $-N-COCH_3$ | $-CH-C_4H_9$ | 6 | 0 | 0 |
| 51 | $-H$ | $-S-$ | $-CH_2-$ | $-CH-CH_3$ | 3 | 1 | 1 |
| 52 | $-CH_3$ | $-SO$ | $-CH_2-$ | — | 0 | 0 | 5 |
| 53 | $-F$ | $-SO_2$ | $-NH$ | — | 8 | 1 | 2 |
| 54 | $-COC_2H_5$ (C=S) | $-C(=O)-$ | $-NH$ | $-CH-C_3H_7$ | 4 | 2 | 2 |

-continued

| | | | | | | |
|---|---|---|---|---|---|---|
| 55 | -CH₂CCH₃ (=O) | -C- (=S) | -NH | -CH= ...pyridinyl-OH | 6 | 1 | 3 |
| 56 | -F | -CH=CH- | -NCH₃ | 3-(CF₃)phenyl-CH- | 2 | 2 | 2 |
| 57 | -H | -C≡C- | -NCH₃ | furan-CH₂CH- | 3 | 4 | 1 |

EXAMPLE 58

Blood was drawn into 0.1 volumes of acid-citrate-dextrose (85 mM sodium citrate, 64 mM citric acid, 110 mM dextrose) by venipuncture from normal human volunteers. Platelet-rich plasma was prepared By centrifugation at 400×g for 12 minutes. PGE1 (5 mg/ml) was added and platelets were collected by centrifugation at 800×g for 12 minutes. The platelet pellet was resuspended into human platelet buffer (140 mM NaCl, 7.9 mM KCl, 3.3 mM $Na_2HPO4$, 6 mM HEPES, 2% bovine serum albumin, 0.1% dextrose, pit 7.2) and filtered over Sepharose 2B that was previously equilibrated in human platelet buffer. Platelets were counted and adjusted to 2×108/ml with human platelet Buffer. Human fibrinogen (10–100 mg/ml and $CaCl_2$ (1 mM) were added and aggregation was initiated by the addition of 10 mM ADP. Aggregation was monitored by the initial rate of increase of light transmittance.

While the invention has been described and illustrated in reference to certain preferred embodiments thereof, those skilled in the art will appreciate that various changes, modifications and substitutions can he made therein without departing from the spirit and scope of the invention. For example, effective dosages other than the preferred doses as set forth hereinabove may he applicable as a consequence of variations in the responsiveness of the mammal Being treated for severity of clotting disorders or emboli, or for other indications for the compounds of the invention indicated above. Likewise, the specific pharmacological responses observed may vary acording to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound selected from the group consisting of:

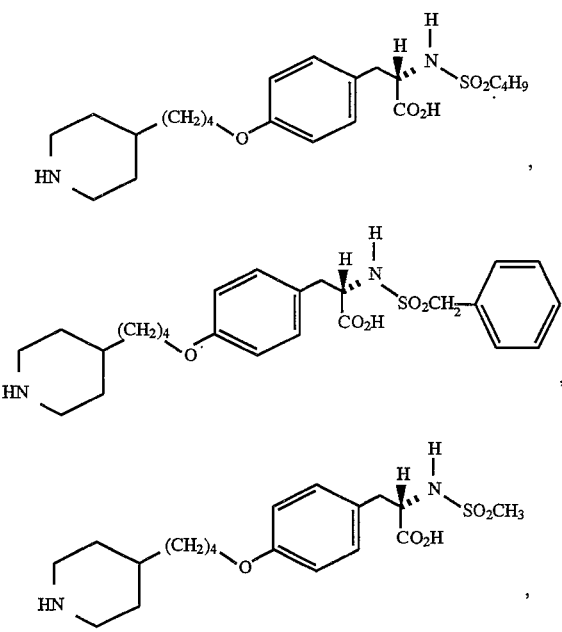

and pharmaceutically acceptable salts thereof.

2. A compound of claim 1 which is

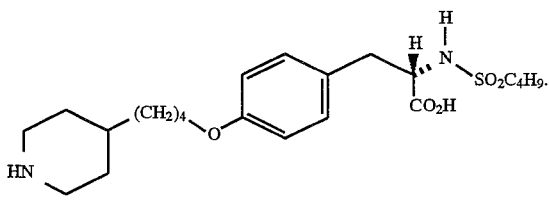

3. A pharmaceutical composition comprising a compound of claim 1 and a pharmaceutically acceptable carrier.

4. A pharmaceutical composition comprising a compound of claim 2 and a pharmaceutically acceptable carrier.

* * * * *